United States Patent [19]

Faraci et al.

[11] Patent Number: 6,005,109
[45] Date of Patent: Dec. 21, 1999

[54] PYRAZOLES AND PYRAZOLOPYRIMIDINES HAVING CRF ANTAGONISTIC ACTIVITY

[75] Inventors: William Stephen Faraci, East Lyme; Willard McKowan Welch, Jr., Mystic, both of Conn.

[73] Assignee: Pfizer Inc., New York, N.Y.

[21] Appl. No.: 08/961,414

[22] Filed: Oct. 30, 1997

Related U.S. Application Data

[60] Division of application No. 08/448,529, filed as application No. PCT/US93/10359, Nov. 3, 1993, Pat. No. 5,712,303, which is a continuation-in-part of application No. 07/992,225, Dec. 17, 1992, abandoned.

[51] Int. Cl.$^6$ .................................................. C07D 471/04
[52] U.S. Cl. ............................................................. 546/119
[58] Field of Search ............................................. 549/119

[56] References Cited

U.S. PATENT DOCUMENTS

| | | |
|---|---|---|
| 3,778,443 | 12/1973 | Arya et al. . |
| 4,337,263 | 6/1982 | Techer et al. . |
| 4,804,675 | 2/1989 | Jensen-Korte et al. . |
| 4,945,165 | 7/1990 | Jensen-Korte et al. . |
| 5,063,245 | 11/1991 | Abreu et al. . |

FOREIGN PATENT DOCUMENTS

| | | |
|---|---|---|
| 2472564 | 3/1981 | France . |

OTHER PUBLICATIONS

T. Nishiwaki et al., "Synthesis of 4–Aroyl–1–arylpyrazoles from alpha–Aroyl–beta–anilinoacrylonitriles and Photochemistry of 4–Carbonyl–substituted Pyrazoles," J. Chem. Soc., Perkin Transactions, No. 15, pp. 1871–1875, 1974.

M. J. Owens et al., "Physiology and Pharmacology of Corticotropin–releasing Factor" Pharmacological Reviews, v. 43, pp. 425–473 (1991).

Chemical Abstracts 106:50185s (1987).

Chemical Abstracts 99:88106s (1983).

Chemical Abstracts 95:43095p (1981).

Chemical Abstracts 89:215295y (1978).

*Primary Examiner*—Patricia L. Morris
*Attorney, Agent, or Firm*—Peter C. Richardson; Paul H. Ginsburg; Jacob M. Levine

[57] ABSTRACT

The pyrazoles and pyzazolopyrimidines of the formula

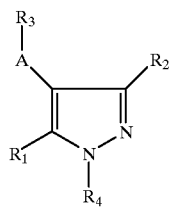

I wherein $R_1$, $R_2$, $R_3$, $R_4$ and A are as defined herein, have corticotropin releasing factor (CRF) antagonist activity. As such, they are effective In the treatment of a wide range of diseases including stress-related illnesses.

4 Claims, No Drawings

PYRAZOLES AND PYRAZOLOPYRIMIDINES HAVING CRF ANTAGONISTIC ACTIVITY

This is a division of application Ser. No. 08/448,529, filed on Jun. 14, 1995, U.S. Pat. No. 5,712,303, which is a national stage application filed pursuant to 35 U.S.C. § 371 of PCT International Application No. PCT/US93/10359, filed Nov. 3, 1993, which is a continuation-in-part of application Ser. No. 07/992,225, filed Dec. 17, 1992, now abandoned.

This invention relates to pyrazoles and pyrazolopyrimidines, pharmaceutical compositions containing them, and methods of administering them to subjects in need of their corticotropin-releasing factor (CRF) antagonist activity. CRF antagonists are mentioned in U.S. Pat. Nos. 4,605,642 and 5,063,245 referring to peptides and pyrazolinones, respectively. The importance of CRF antagonists is set out in the literature, e. g. as discussed in U.S. Pat. No. 5,063,245, which is Incorporated herein by reference. A recent outline of the different activities possessed by CRF antagonists is found in M. J. Owens et al., Pharm. Rev., Vol. 43, pages 425 to 473 (1991), also incorporated herein by reference. Based on the research described in these two and other references, CRF antagonists are effective in the treatment of a wide range of diseases including stress-related illnesses, such as stress- induced depression, anxiety, and headache; abdominal bowel syndrome; inflammatory diseases; immune suppression; human immunodeficiency virus (HIV) infections; Alzheimer's disease; gastrointestinal diseases; anorexia nervosa; hemorrhagic stress; drug and alcohol withdrawal symptoms; drug addiction, and fertility problems.

The compound of formula I below wherein A is C=O, $R_1$ is amino, $R_2$ is methylthio, $R_3$ is 2-chlorophenyl, and $R_4$ is 2,4,6-trichlorophenyl is a commercial compound of no known utility.

The present invention relates to a compound of the formula

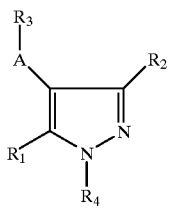

I and the acid addition salts thereof, wherein

A is C=O or $SO_2$, or A and $R_1$ together with the carbons to which they are attached form pyrimidinyl or 5-pyridyl which may be substituted by $R_6$ which is hydrogen, $C_1$–$C_6$ alkyl, fluoro, chloro, bromo, hydroxy, amino, O($C_1$–$C_6$ alkyl), NH($C_1$–$C_6$ alkyl), N($C_1$–$C_6$ alkyl)($C_1$–$C_6$ alkyl), SH, S(O)$_n$($C_1$–$C_6$ alkyl) wherein n=0, 1 or 2. wherein said $C_1$–$C_6$ alkyl may be substituted by from 1 to 3 substituents $R_6$ which is hydroxy, amino, $C_1$–$C_3$ alkoxy, dimethylamino, diethylamino, methylamino, ethylamino, NH(C=O)CH$_3$, fluoro, chloro, bromo or $C_1$–$C_3$ thioalkyl;

$R_1$ is hydrogen, $C_1$–$C_6$ alkyl, amino, O($C_1$–$C_6$ alkyl), NH($C_1$–$C_6$ alkyl), N($C_1$–$C_6$ alkyl)($C_1$–$C_6$ alkyl), wherein said $C_1$–$C_6$ alkyl may be substituted by from 1 to 3 substituents $R_6$ as defined above;

$R_2$ Is hydrogen, $C_1$–$C_6$ alkyl, hydroxy, amino, O($C_1$–$C_6$ alkyl), NH($C_1$–$C_6$ alkyl), N($C_1$–$C_6$ alkyl)($C_1$–$C_6$ alkyl), SH, S(O)$_n$($C_1$–$C_6$ alkyl) wherein n=0, 1, or 2, cyano, hydroxy, carboxy, or amido, wherein said alkyls may be substituted by one to three of hydroxy, amino, carboxy, amido, NH(C=O) ($C_1$–$C_6$ alkyl), N($C_1$–$C_6$ alkyl)($C_1$–$C_6$ alkyl), (C=O)O ($C_1$–$C_6$ alkyl), $C_1$–$C_3$ alkoxy, $C_1$–$C_3$ thioalkyl, fluoro, bromo, chloro, iodo, cyano or nitro;

$R_3$ is phenyl, naphthyl, thienyl, benzothienyl, pyridyl, quinolyl, pyrazinolyl, pyrimidyl, imidazolyl, furanyl, benzofuranyl, benzothiazolyl, isothiazolyl, benzoisothiazolyl, thiazolyl, isoxazolyl, benzisoxazolyl, benzimidazolyl, triazolyl, pyrazolyl, pyrrolyl, indolyl, azaindolyl, benzoxazolyl, oxazolyl, pyrrolidinyl, thiazolidinyl, morpholinyl, pyridinyl, tetrazolyl, or 9 to 12 membered bicycloalkyl, optionally containing one to three of O, S or N-Z wherein Z is hydrogen, $C_1$–$C_4$ alkyl, $C_1$–$C_4$ alkanoyl, phenyl or phenylmethyl, wherein each one of the above groups may be substituted independently by from one to three of fluoro, chloro, bromo, $C_1$–$C_6$ alkyl, $C_1$–$C_6$ alkoxy, or trifluoromethyl, or one of cyano, nitro, amino, NH($C_1$–$C_6$ alkyl), N($C_1$–$C_4$ alkyl)($C_1$–$C_2$ alkyl), COO ($C_1$–$C_4$ alkyl), CO($C_1$–$C_4$ alkyl), SO$_2$NH($C_1$–$C_4$ alkyl), SO$_2$N($C_1$–$C_4$ alkyl)($C_1$–$C_2$ alkyl), SO$_2$NH$_2$, NHSO$_2$($C_1$–$C_4$ alkyl), S($C_1$–$C_6$ alkyl), SO$_2$($C_1$–$C_6$ alkyl), wherein said $C_1$–$C_4$ alkyl and $C_1$–$C_6$ alkyl may be substituted by one or two of fluoro, chloro, hydroxy, amino, methylamino, dimethylamino or acetyl; and $R_4$ is phenyl, naphthyl, thienyl, benzothienyl, pyridyl, quinolyl, pyrazinolyl, pyrimidyl, imidazolyl, furanyl, benzofuranyl, benzothiazolyl, isothiazolyl, benzoisothiazolyl, thiazolyl, isoxazolyl, benzisoxazolyl, benzimidazolyl, triazolyl, pyrazolyl, pyrrolyl, indolyl, azaindolyl, benzoxazolyl, oxazolyl, pyrrolidinyl, thiazolidinyl, morpholinyl, pyridinyl, tetrazolyl, or 3 to 8-membered cycloalkyl or 9 to 12-membered bicycloalkyl, optionally containing one to three of O, S or N-Z wherein Z is hydrogen, $C_1$–$C_4$ alkyl, $C_1$ –$C_4$ alkanoyl, phenyl or phenylmethyl, wherein each of the above groups may be substituted independently by from one to three of fluoro, chloro, bromo, trifluoromethyl, $C_1$–$C_6$ alkyl or $C_1$–$C_6$ alkoxy, or one of cyano, nitro, amino, NH($C_1$–$C_6$ alkyl), N($C_1$–$C_4$ alkyl)($C_1$–$C_2$ alkyl), COO($C_1$–$C_4$ alkyl), CO($C_1$–$C_4$ alkyl), SO$_2$NH($C_1$–$C_4$ alkyl), SO$_2$N($C_1$–$C_4$ alkyl)($C_1$–$C_2$ alkyl), SO$_2$NH$_2$, NH$_2$SO$_2$($C_1$–$C_4$ alkyl), S($C_1$–$C_6$ alkyl), SO$_2$($C_1$–$C_6$ alkyl), wherein said $C_1$–$C_4$ alkyl and $C_1$–$C_6$ alkyl may be substituted by one or two of fluoro, chloro, hydroxy, amino, methylamino, dimethylamino or acetyl; provided that (1) $R_4$ is not unsubstituted phenyl; (2) when $R_1$ is amino, $R_2$ is methylthio, $R_4$ is 2,4,6-trichlorophenyl, and A is C=O, then $R_3$ is not 2-chlorophenyl; and (3) $R_1$ and $R_2$ are not both hydrogen.

More specific compounds of the formula I Include those wherein $R_3$ is phenyl substituted independently with one or two of fluoro, chloro, bromo, methyl, trifluoromethyl, nitro, $C_1$–$C_6$ alkyl, $C_1$–$C_6$ alkyloxy, SO$_2$NH$_2$,SO$_2$NH($C_1$–$C_6$ alkyl), SO$_2$N($C_1$–$C_6$ alkyl)$_{21}$ or $R_3$ is primary, secondary or tertiary alkyl of from 4–9 carbon atoms wherein said $C_4$–$C_9$ alkyl may contain from one to two double or triple bonds and may be substituted by from 1 to 3 substituents $R_6$ which is hydroxy, amino, $C_1$–$C_3$ alkoxy, dimethylamino, diethylamino, methylamino, ethylamino, NH(C=O)CH$_3$, fluoro, chloro, bromo, or $C_1$–$C_3$ thioalkyl.

More specific compounds of the formula I are those wherein A is C=O, those wherein $R_1$ is amino, methylamino or dimethylamino; those wherein $R_2$ is ethyl or methylthio and those wherein $R_4$ is 2,4,6-trichlorophenyl, 2,4,6-trimethylphenyl, 2,6-dichloro-4-trifluoromethylphenyl or 4-bromo-2,6-dimethylphenyl.

More specific compounds of formula I further include those wherein $R_3$ is phenyl which may be substituted at positions 2 or 5 with one or two of methyl, $C_2$–$C_6$ straight-chain or branched alkyl, trifluoromethyl, fluoro, chloro, bromo or nitro, those wherein A and $R_1$ together form a pyrimidine ring, such that the bicyclic structure formed is pyrazolo[3,4]pyrimidine, and $R_6$ is substituted at the 6 position; and those wherein $R_3$ is phenyl substituted independently with one or two of fluoro, chloro, bromo, methyl, trifluoromethyl, nitro, $C_1$–$C_6$ alkyl, $C_1$–$C_6$ alkyloxy, $SO_2NH_2$, $SO_2NH(C_1$–$C_6$ alkyl), or $SO_2N(C_1$–$C_6$ alkyl)$_2$, $R_4$ is 2,4,6trichlorophenyl, 2,4,6-trimethylphenyl, 2,6-dichloro-4-trifluoromethylphenyl or 4-bromo-2,6dimethylphenyl, and $R_2$ is methylthio, methyl or ethyl.

More specific compounds of formula I also include those wherein $R_3$ is phenyl substituted independently with one or two of fluoro, chloro, bromo, methyl, trifluoromethyl, nitro, $C_1$–$C_6$ alkyl, $C_1$–$C_6$ alkyloxy, $SO_2NH_2$, $SO_2NH(C_1$–$C_6$ alkyl), $SO_2N(C_1$–$C_6$ alkyl)$_2$ or $R_3$ is primary, secondary or tertiary alkyl of from 4–9 carbon atoms wherein said $C_4$–$C_9$ alkyl may contain from one to two double or triple bonds and may be substituted by from 1 to 3 substituents $R_6$ which is hydroxy, amino, $C_1$–$C_3$ alkoxy, dimethylamino, diethylamino, methylamino, ethylamino, $NH(C=O)CH_3$, fluoro, chloro, bromo or $C_1$–$C_3$ thioalkyl; $R_4$ is 2,4,6-trichlorophenyl, 2,4,6trimethylphenyl, 2,6-dichloro-4-trifluoromethylphenyl or 4-bromo-2,6-dimethylphenyl; $R_1$ is amino, methylamino or dimethylamino; and $R_2$ is methylthio or ethyl.

The most preferred compounds of the invention are

[5-amino-1-(2,6-dichloro-4-trifluoromethylphenyl)-3-methylsulfanyl-1H-pyrazol-4-yl]-(2,5-dimethylphenyl) methanone,

[5-amino-1-(2,6-dichloro-4-trifluoromethylphenyl)-3-methylsulfanyl-1H-pyrazol-4-yl]-(2,5-bis-trifluoromethylphenyl)methanone,

[5-amino-1-(2,6-dichloro-4-trifluoromethylphenyl)-3-methylsulfanyl-1H-pyrazol-4-yl]-(2,5-isopropyl-2-methylphenyl)methanone,

[5-amino-3-methylsulfanyl-1-(2,4,6-trichlorophenyl)-1H-pyrazol-4-yl]-(5-isopropyl-2-methylphenyl)methanone, and

[5-amino-1-(4-bromo-2,6-dimethylphenyl)-3-methylsulfanyl-1H-pyrazol-4-yl]-(2,5-dibromophenyl) methanone.

The invention also relates to a composition for the treatment of illnesses induced or facilitated by corticotropin releasing factor which comprises a compound of the formula I as defined above or the known compound of formula I wherein A is C=O, $R_1$ is amino, $R_2$ is methylthio, $R_3$ is 2-chlorophenyl, and $R_4$ is 2,4,6trichlorophenyl, in an amount effective in the treatment of said illnesses, and a pharmaceutically acceptable carrier, and to a composition for the treatment of inflammatory disorders, stress and anxiety related disorders including stress-induced depression and headache, abdominal bowel syndrome, immune supression, HIV infections, Alzheimer's disease, gastrointestinal diseases, anorexia nervosa, hemorrhagic stress, drug and alcohol withdrawal symptoms, drug addiction, and fertility problems, which comprises a compound of the formula I as well as the known compound, both as defined above in an amount effective in the treatment of said disorders, and a pharmaceutically acceptable carrier. More specific and most preferred compositions for the treatment of such illnesses and disorders comprise a more specific and most preferred compound of formula I as defined above.

The invention further Includes a method for the treatment of illnesses induced or facilitated by corticotropin releasing factor by administering to a subject in need of such treatment a compound of formula I or the known compound, both as defined above, and a method for the treatment of stress and anxiety related disorders, including stress-induced depression and headache, abdominal bowel syndrome, Inflammatory disorders, Immune suppression, HIV infections, Alzheimer's disease, gastrointestinal diseases, anorexia nervosa, hemorrhagic stress, drug and alcohol withdrawal symptoms, drug addiction, and fertility problems, particularly depression, by administering to a subject in need of such treatment a compound of formula I as well as the known compound, both as defined above. More specific and most preferred methods for the treatment of such illnesses and disorders comprise a more specific and most preferred compound of formula I as described above.

Whenever reference is made herein to $C_1$–$C_6$ alkyl, a straight or branched chain alkyl of one to six carbon atoms is meant, such as methyl, ethyl, isopropyl or hexyl.

Whenever reference Is made herein to $C_1$–$C_6$ alkyl, in the definition of $R_5$ and $R_1$, this includes unsaturated $C_2$–$C_6$ alkyl, such as $C_2$–$C_6$ alkyl having one double or triple bond, $C_3$–$C_6$ alkyl having two double bonds, and $C_4$–$C_6$ alkyl having two triple bonds.

Whenever reference is made hereafter to a compound of formula I, this includes the known compound of formula I as described above.

Whenever $R_3$ is a heterocyclic group, the attachment to A, defined above, is through one of the carbons in the heterocyclic group. Similarly, when $R_4$ is a heterocyclic group, the attachment to the nitrogen in the pyrazole ring is through one of the carbons in the heterocyclic group.

Whenever reference is made herein to 3–8 membered cycloalkyl or 9- to 12-membered bicycloalkyl containing one to three of O, S or N-Z, it is understood that the oxygen and sulfur ring atoms are not adjacent to each other.

The compounds of the formula I wherein $R_1$ is amino or $C_1$–$C_6$ alkyl, and $R_2$ is methylthio, having the formula II (not shown), may be prepared from a compound of the formula

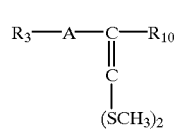

III wherein $R_{10}$ is cyano or $C(O)(C_1$–$C_6$ alkyl) and A and $R_3$ are as defined above with reference to formula I, by reaction with a compound of the formula

     IV wherein $R_4$ is as defined with reference to formula I. This reaction is generally carried out in a polar solvent, such as a $C_1$–$C_6$ alcohol. The reaction temperature generally ranges from about 20° C. to about 160° C., and is conveniently the reflux temperature of the reaction mixture.

The compounds of formula III may be prepared by treating a compound of the formula

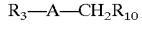     V with a base such as sodium hydride, in the presence of carbon disulfide followed by reaction of the formed intermediate with methyl iodide in a reaction solvent such as dimethylsulfoxide.

The compounds of formula IV are readily available or may be obtained by methods known in the art.

The compounds of formula V may be prepared by known methods.

The compounds of the formula I wherein $R_2$ is alkoxy, amino, or mono- or disubstituted amino may be prepared by using the above procedure with $R_4NHNH_2$ from the corresponding compounds of the formula

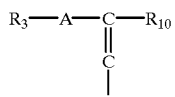

OR

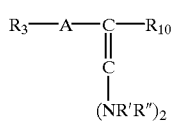

wherein A and $R_3$ are as defined with reference to formula I, $R_{10}$ is as defined with reference to formula III, and R, R' and R" are each hydrogen or $C_1$–$C_6$ alkyl in accordance with the definition of $R_2$ above.

The compounds of the formula I wherein $R_1$ is $C_1$–$C_6$, alkoxy or $C_1$–$C_6$ alkylthio and $R_2$ is $C_1$–$C_6$ alkyl may be prepared from a compound of the formula

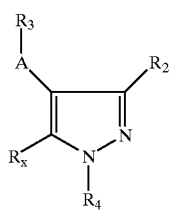

IX wherein $R_X$ is chloro or bromo, $R_2$ is $C_1$–$C_6$ alkyl, and $R_3$, $R_4$ and A are as defined above with reference to formula I, with a $C_1$–$C_6$ alcohol or $C_1$–$C_6$ mercaptan in the presence of a base. The reaction is generally carried out in a polar solvent such as ethanol or t-butanol at temperatures from about 20° C. to about 160° C. and conveniently room temperature.

The compounds of the formula IX may be prepared by treating a compound of the formula

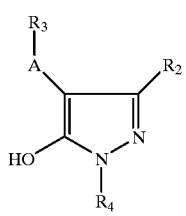

X with a halogenating agent such as thionyl chloride or bromide, or phosphorous oxychloride or pentachloride, or phosphorous oxybromide or pentabromide. The reaction may be carried out without a solvent or in an aprotic solvent such as methylene chloride, or dichloroethane at temperatures of about 0° C. to about 100° C.

Compounds of formula X may be prepared by treating compounds of the formula

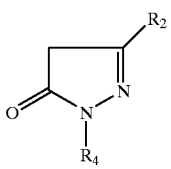

XI with an activated derivative of a carboxylic or sulfonic acid of the formula $R_3AOH$, such as an acid chloride of the formula $R_3ACl$ wherein $R_3$ and A are as defined with reference to formula I, in the presence of calcium hydroxide in an aprotic solvent such as dioxane as described in Jensen, Acta Chem. Scand., 13, 1668–1670 (1959) at temperatures of from about 20° C. to about 100° C. Compounds of the formula XI are known in the art.

The compounds of the formula I wherein $R_1$ is $C_1$–$C_6$ alkoxy or $C_1$–$C_6$ alkylthio and $R_2$ is $C_1$–$C_6$ alkylthio may be prepared from a compound of the formula

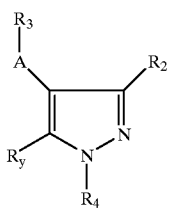

XII wherein $R_Y$ is chloro or bromo and $R_3$, $R_4$ and A are as defined above with reference to formula I, with a $C_1$–$C_6$ alcohol or $C_1$–$C_6$ mercaptan in the presence of a base. The reaction is generally carried out in a polar organic solvent such as ethanol or t-butanol at temperatures from about 20° C. to about 160° C., conveniently room temperature.

The compounds of the formula XII may be prepared from a compound of the formula

XIII by reaction with a halogenating agent such as thionyl chloride or bromide, or phosphorous oxychloride or pentachloride, or phosphorous oxybromide or pentabromide. The reaction may be carried out with a solvent or in an aprotic solvent such as methylene chloride or dichloroethane at temperatures of about 0° C. to about 100° C.

The compounds of the formula XIII may be prepared by treating a compound of the formula

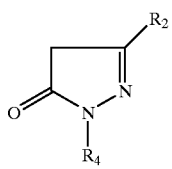

XIV with activated benzoic or sulfonic acid derivatives, conveniently an acid chloride, in the presence of calcium hydroxide in an aprotic solvent such as dioxane as described in the above reference by Jensen.

The compounds of the formula XIV may be prepared by treating a compound of the formula

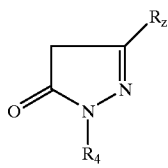

XV wherein $R_2$ is chloro, bromo with a $C_1$–$C_6$ mercaptan in the presence of a base. The reaction is generally carried out in a polar organic solvent such as t-butanol at temperatures from about 20° C. to about 160° C., conveniently the reflux temperatures of the reaction mixture.

The compounds of the formula XV may be prepared from compounds of the formula

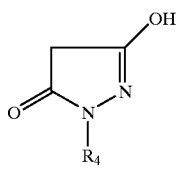

XVI with a halogenating agent such a thionyl chloride or bromide, or phosphorous oxychloride or pentachloride, or phosphorous oxybromide or pentabromide. The reaction may be carried out without a solvent or in an aprotic solvent such as methylene chloride or dichloroethane at temperatures of about 0° C. to about 100° C.

The compounds of the formula I wherein $R_1$ is $C_1$–$C_6$ alkoxy or $C_1$–$C_6$ alkylthio and $R_2$ is $C_1$–$C_6$ alkoxy may be prepared from a compound of the formula

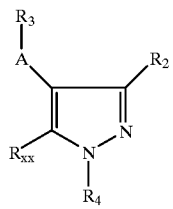

XVII wherein $R_{xx}$ is chloro or bromo, $R_2$ is $C_1$–$C_6$ alkoxy and $R_3$, $R_4$ and A are as defined above with reference to formula I, with a $C_1$–$C_6$ alcohol or $C_1$–$C_6$ mercaptan in the presence of a base. The reaction is generally carried out in a polar organic solvent such as ethanol or t-butanol at temperatures from about 20° C. to about 160° C., conveniently the reflux temperature of the reaction mixture.

The compounds of the formula XVII may be prepared from a compound of the formula

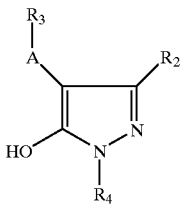

XVIII by reaction with a halogenating agent such as thionyl chloride or bromide, or phosphorous oxychloride or pentachloride, or phosphorous oxybromide or pentabromide. The reaction may be carried out without a solvent or in an aprotic solvent such as methylene chloride, or dichloroethane at temperatures of about 0° C. to about 100° C.

The compounds of the formula XVIII may be prepared by treating a compound of the formula

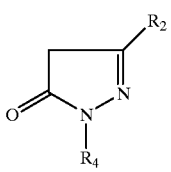

XIX with an activated derivative of a carboxylic or sulfonic acid of the formula $R_3AOH$, conveniently an acid chloride of the formula $R_3ACl$ wherein $R_3$ and A are as defined above with reference to formula I, in the presence of calcium hydroxide in an aprotic solvent such a dioxane as described by Jensen in the reference cited above.

The compounds of the formula XIX may be prepared by treating a compound of the above formula XV with an alcohol in the presence of a base. The reaction is generally carried out in a polar organic solvent such as ethanol at temperatures from about 20° C. to about 160° C., conveniently the reflux temperatures of the reaction mixture.

The compounds of the formula I wherein $R_1$ is amino and $R_2$ is $O(C_1$–$C_6$ alkyl) may be prepared by reacting a compound of the formula

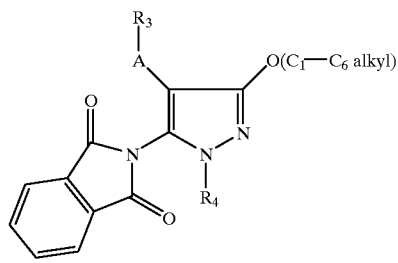

XX wherein $R_3$, $R_4$ and A are as defined above with reference to formula I, with hydrazine in a solvent such as a $C_1$–$C_6$ alcohol, conveniently at the boiling point of the solvent.

The compounds of the formula XX may be prepared by treating a compound of the formula

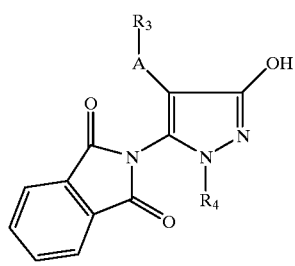

XXI wherein $R_3$, $R_4$ and A are as defined above with reference to formula I, with an alkylating agent such as di($C_1$–$C_6$ alkyl) sulfate, and a base such as sodium hydride, in a solvent such as dimethylsulfoxide.

The compounds of the formula XXI may be prepared by treating a compound of the formula

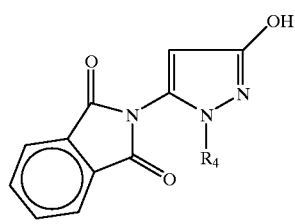

XXII with an activated derivative of a carboxylic or sulfonic acid of the formula $R_3AOH$ such as an acid chloride of the formula $R_3ACl$, wherein $R_3$ and A are as defined with reference to formula I, in the presence of a Lewis acid such as aluminum chloride in an aprotic solvent such as methylene chloride, dichloroethane, or tetrachloroethane, at temperatures of about 0° C. to about 150° C.

The compounds of the formula XXII may be prepared by treatment of a compound of the formula

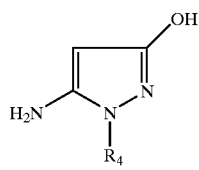

XXIII with phthalic anhydride in acetic acid at the boiling point of the solvent.

The compounds of the formula XXIII may be prepared by contacting cyanoacetyl chloride with $R_4NHNH_2$ in the presence of a base followed by heating the resulting hydrazide at reflux in alcoholic solution in the presence of a base.

The compounds of formula I wherein A and $R_1$ are taken together to form pyrimidinyl have the formula

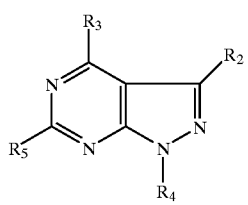

XXIV wherein $R_2$, $R_3$, $R_4$, and $R_5$ are as defined above with reference to formula I. These compounds may be prepared by cyclization of a compound of the above formula I wherein A is C=O and $R_1$ is amino with a compound of the formula

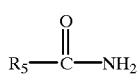

XXV wherein $R_5$ is as defined with reference to formula I. This reaction is generally carried out at 100 to 250° C., and conveniently at the reflux temperature of the compound XXV.

The compounds of formula I wherein A and $R_1$ are taken together to form 5-pyridyl have the formula

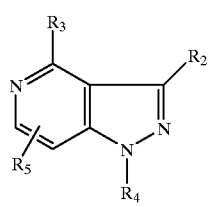

XXVI wherein $R_2$, $R_3$, $R_4$ and are as defined with reference to formula I. These compounds may be prepared as shown in Reaction Scheme 1.

Reaction Scheme 1

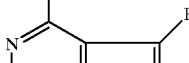

XXVII     XXVIII

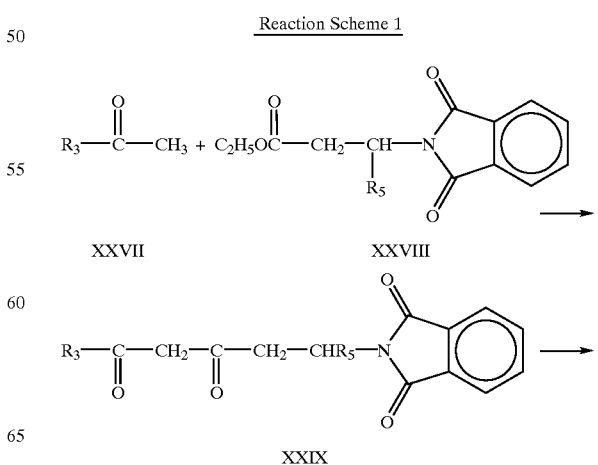

XXIX

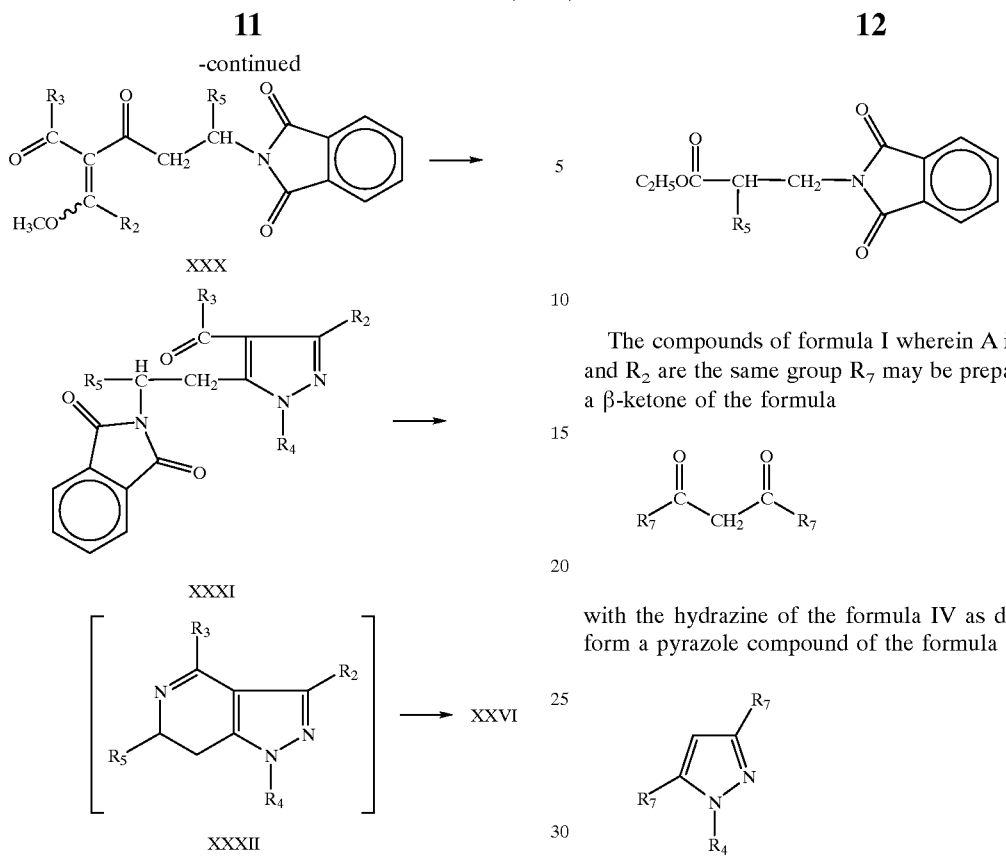

The compounds of formula XXIX are prepared by reacting a ketone of the formula XXVII with a compound of the formula XXVIII in a suitable solvent such as tetrahydrofurane in the presence of a base such as sodium hydride. The reaction is conveniently carried out at the reflux temperature of the reaction mixture.

The compound XXIX is reacted with a compound of the formula $R_2C(OCH_3)_3$ to form the compound XXX. The reaction is carried out in a suitable solvent such as ethyl acetate, conveniently at the reflux temperature of the reaction mixture. The wavy line in formula XXX indicates that either isomer of this compound is included, in accordance with accepted convention for indicating stereoisomers.

The compound XXXI is prepared by reacting compound XXX with a hydrazine of the formula $H_2NNHR_4$ wherein $R_4$ is as defined with reference to formula I. The reaction is carried out in a suitable solvent such as ethanol, conveniently at the reflux temperature of the reaction mixture.

The compounds of formula XXVI wherein $R_5$ is linked to position 6 is formed by first reacting compound XXXI with hydrazine hydrate in a suitable solvent such as ethanol, conveniently at the reflux temperature of the reaction mixture. The compound XXXII is separated from precipitated phthalhydrazide and taken up in an organic solvent such as toluene. The compound XXVI is formed by dehydrogenation of compound XXXII with palladium over carbon.

Reaction Scheme 1 shows the preparation of compounds XXVI wherein $R_5$ is in the 6-position. A similar reaction sequence may be followed to prepare compounds XXVI wherein $R_5$ is in the 7-position by replacing compound XXVII by a compound of the formula

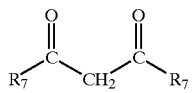

The compounds of formula I wherein A is C=O and $R_1$ and $R_2$ are the same group $R_7$ may be prepared by reacting a β-ketone of the formula

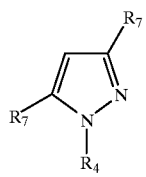

with the hydrazine of the formula IV as defined above to form a pyrazole compound of the formula

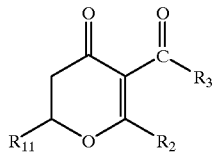

The reaction proceeds at reflux in an appropriate solvent such as ethanol. After bromination of the pyrazole compound, e.g. with bromine in acetic acid, to form the corresponding 4-bromo derivative and conventional metallation, e.g. with t-butyl lithium, at −78° C. in tetrahydrofuran, a suitably activated $R_3$ carboxylic acid such as the acid chloride $R_3C(O)Cl$ is added to give the desired compound 1.

The compounds of formula I wherein A is C=O and $R_1$ and $R_2$ are not the same, and wherein $R_1$ or $R_2$ is attached through a $C_2H_4$ fragment, may be prepared from a pyranone of the formula

XXXIV wherein $R_3$ is as defined above, and $R_2$ is as defined above when $R_{11}$ is $C_3$–$C_6$ alkyl which may be substituted by 1 to 3 of $R_6$, or $R_2$ is $R_1$ when $R_{11}$ is $C_3$–$C_6$ alkyl which may be substituted by one to three of hydroxy, amino, carboxy, amido, NH(C=O)($C_1$–$C_6$ alkyl), N($C_1$–$C_6$ alkyl)($C_1$–$C_6$ alkyl), (C=O)O($C_1$–$C_6$), $C_1$–$C_3$ alkoxy, $C_{13}$ thioalkyl, fluoro, bromo, chloro, iodo, cyano or nitro. The compound XXXIV is reacted with a hydrazine of the formula $H_2NNHR_4$ wherein $R_4$ is as defined above to form compounds of the formulae

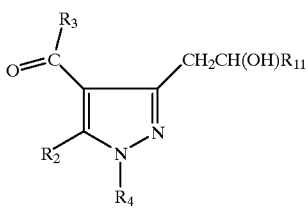

and

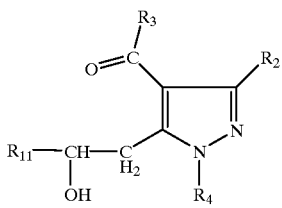

which on dehydration and hydrogenation result in compounds of the formulae

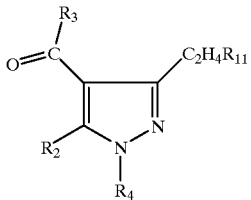

and

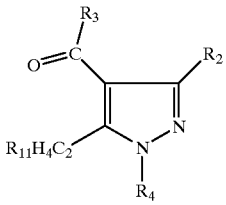

The compounds of the formula I wherein A is C=O and $R_2$ is $O(C_1-C_6$ alkyl) may be prepared by reacting a hydrazine of the formula $R_4NHNH_2$ with a compound of the formula (A) in a suitable solvent

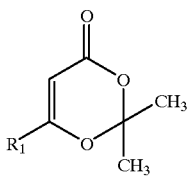

(A)

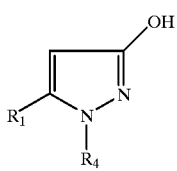

(B)

such as THF or methylene chloride and cyclization of the resulting hydrazide with heat to give the intermediate (B). This compound may be reacted with an activated carboxylic acid derivative such as the acid chloride $R_3(C=O)Cl$ in the presence of a Lewis acid such as aluminum trichloride in a solvent such as ethylene dichloride at temperatures of from about $-10°$ C. to about $80°$ C. The formed compound of formula I wherein $R_2$ is hydroxy may be reacted with $(C_1-C_6$ alkyl)L wherein L is a leaving group such as chloro, bromo, or tosylate and $C_1-C_6$ alkyl may be substituted in accordance with the substituents in the definition of $R_2$.

Those compounds of formula I wherein $R_1$ is $C_1-C_6$ alkylamino or di($C_1-C_6$ alkyl)amino may be prepared from corresponding compounds of formula I wherein $R_1$ is amino. When R, is methylamino or dimethylamino, reaction is with a methylating agent such as methyl iodide. When $R_1$ is $C_2-C_6$ alkylamino or di($C_2-C_6$ alkyl)amino, reaction is with an alkylating agent such as $C_2-C_6$ alkyl-L wherein L is a leaving group such as chloro, bromo, tosylate, or mesylate. Both the methylation and the $C_2-C_6$ alkylation is in the presence of a base such as sodium hydride and a solvent such as tetrahydrofuran, dimethyl formamide or dimethyl sulfoxide.

The acid addition salts are prepared in a conventional manner by treating a solution or suspension of the free base of formula I with one chemical equivalent of a pharmaceutically acceptable acid. Conventional concentration or crystallization techniques are employed in isolating the salts. Illustrative of suitable acids are acetic, lactic, succinic, maleic, tartaric, citric, gluconic, ascorbic, benzoic, cinnamic, fumaric, sulfuric, phosphoric, hydrochloric, hydrobromic, hydroiodic, sulfamic, sulfonic acids such as methanesulfonic, benzene sulfonic, p-toluenesulfonic, and related acids.

The compound of the invention may be administered alone or in combination with pharmaceutically acceptable carriers, in either single or multiple doses. Suitable pharmaceutical carriers Include Inert solid diluents or fillers, sterile aqueous solution and various organic solvents. The pharmaceutical compositions formed by combining the novel compounds of formula I and the pharmaceutically acceptable carriers are then readily administered in a variety of dosage forms such as tablets, powders, lozenges, syrups, Injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral administration, solutions of the novel compound of formula I in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. The sterile aqueous media employed are all readily available by standard techniques known to those skilled in the art.

Additionally, it is possible to administer the compounds of the present invention topically when treating inflammatory conditions of the skin and this may be done by way of creams, jellies, gels, pastes and ointments, in accordance with standard pharmaceutical practice.

The effective dosage for the compound of formula I depends on the intended route of administration and other factors such as age and weight of the patient, as generally known to a physician. The dosage also depends on the illness to be treated, although in general the daily dosage will range from about 0.1 to 50 mg/kg of the body weight of the patient. More specifically, the daily dosage for stress-induced illnesses will generally range from about 0.1 to 50 mg/kg of the body weight of the patient to be treated, for treatment of inflammatory diseases about 0.1 to about 100 mg/kg will be needed, for Alzheimer's disease, about 0.1 to about 50 mg/kg, as well as for gastrointestinal diseases, anorexia nervosa, hemorrhagic stress, and drug and alcohol withdrawal symptoms.

The methods for testing the compounds for formula I for their CRF antagonist activity are according to the procedures of Endocrinology, 116, 1653–1659 (1985) and Peptides, 10, 179–188 (1985) which determine the binding activity of a test compound to a CRF receptor. The binding activity for the compounds of formula I generally ranges from about 0.2 nanomolar to about 10 micromolar.

The following abbreviations are used in the Examples: Ph=phenyl; iPr=isopropyl; HRMS=high resolution mass spectrum.

EXAMPLE 1

A. 2-Bromo-2',5'-dimethylacetophenone

A mixture of 10.60 g (0.10 mol) of para-xylene and 16.53 g (0.105 mol) of α-bromoacetyl chloride in 300 mL of 1,2-dichloroethane was cooled in an ice bath under an atmosphere of dry $N_2$ and treated portionwise with 14.15 g (0.106 mol) of aluminum chloride. The reaction mixture was stirred for 30 minutes at 0–5° C. and then for 2.5 hours at room temperature. The mixture was then poured onto ice and the aqueous layer was acidified with concentrated HCl. The organic layer was separated and the aqueous layer was extracted twice with methylene dichloride. The combined organic extracts were dried with brine solution and with magnesium sulfate. The solvent was evaporated to give 23.87 g of an amber oil which was for use in the next reaction without further purification.

B. 2-Cyano-2',5'-dimethylacetophenone

The product of the above reaction (approximately 0.10 mol) was dissolved in 300 mL of ethanol and was treated with a solution of 16.25 g (0.25 mol) of potassium cyanide in 30 mL of water and the resulting mixture was refluxed for 90 minutes. After cooling, the ethanol was stripped from the mixture on the rotary evaporator and the residues were made slightly acidic with concentrated hydrogen chloride. The product was extracted Into ethyl acetate using precautions to avoid escape of hydrogen cyanide. The organic extracts were dried with brine and with magnesium sulfate and 5 evaporated to a gummy semi-solid. This was triturated repeatedly with hot hexane which, on cooling, deposited needles to give the desired product, 8.50 g (49% for the two reactions), m.p. 75–76° C.

C. 3,3-Bis-methylthio-2-(2(2,5-dimethylbenzoyl-acreylonitrile

A solution of 4.96 g (28.6 mmol) of 2-cyano-2',5'-dimethylacetophenone in 120 mL of dry dimethyl sulfoxide and 3.43 mL (57.3 mmol) of carbon disulfide in a flame-dried 3-neck round bottom flask under dry nitrogen was stirred at 15–18° C. while 1.41 g (58.7 mmol) of oil free sodium hydride was added in 5 portions. The resulting deep red solution was stirred for 1 hour at 18° C. and then cooled to 15° C. whereupon 3.92 mL (8.95 g, 63.0 mmol) of methyl iodide was added dropwise. The temperature rose to about 22° C. during the addition. After stirring for 2 hours at room temperature, the reaction mixture was poured into cold water and the aqueous layer was extracted three times with ethyl acetate. The combined extracts were washed three times with water and then dried with brine and magnesium sulfate. Evaporation gave 8.96 g of the title compound as a heavy orange oil which crystallized in the refrigerator. The analytical sample crystallized from ethanol, m.p. 74.5–75.5° C.

D. Amino-1-(2,6-dichloro-4-trifluoromethylphenyl)-4-(2,5-dimethylbenzoyl)-3-methylthiopyrazole A suspension of 7.94 g (28.6 mmol) of the product of step C and 7.01 g (28.6 mmol) of 2,6-dichloro-4-trifluoromethylphenylhydrazine in 100 mL of ethanol was heated at reflux for 2 hours, solution occurring as the reaction mixture was warmed. Then the ethanol was mostly removed on the rotary evaporator and the residues were partitioned between dilute aqueous hydrogen chloride solution and ethyl acetate. The organic phase was washed once with water and with brine, then dried with magnesium sulfate and treated with decolorizing carbon. The filtered solution was evaporated and the residues crystallized from 10:1 hexane/ethyl acetate to give 12.00 g (88%) of the title product in two crops, m.p. 130–132° C.

EXAMPLE 2

5-Methylamino-4(2-chlorobenzoyl)-3-methylthio-1-(2,4,6-trichlorophenyl)pyrazole and 5-dimethylamino-4-(2-chlorobenzoyl)-3-methylthio-1-(2,4,6-trichlorophenyl)-pyrazole A mixture of 0.50 g (1.16 mmol) of 5-amino-4-(2-chlorobenzoyl)-3-methylthio-1-(2,4,6-trichlorophenyl)pyrazole in 5 mL of tetrahydrofuran was treated with 50 mg (1.16 mmol) of sodium hydride and stirred at room temperature for 30 minutes. Then 0.75 ml (1.71 g, 12.0 mmol) of methyl iodide was added dropwise and the reaction mixture was stirred for 60 minutes at room temperature. The reaction mixture was then quenched with water and the products were extracted into ethyl acetate. Concentration of the dried solution and chromatography on silica gel with mixture of hexane and ethyl acetate gave the less polar dimethylamino title compound (300 mg, 54%) as a white foam. Anal. Calcd. for $C_{19}H_{15}ON_3SCl_4$: C, 48.02; H, 3.18; N, 8.88. Found: C, 47.84; H, 3.09; N, 9.01.

The more polar monomethyl title compound was isolated from the column in like manner as a white foam (34 mg, 6%). Anal. Calcd. for $C_{18}H_{13}ON_3SCl_4$: C, 46.88; H, 2.84; N, 9.11. Found: C, 46.54; H, 2.89; N, 9.07.

EXAMPLE 3

45-Amino-4-(2-methoxybenzoyl)-3-methylthio-1-(2,4,6-trichlorophenyl)pyrazole

To a solution of 2-methoxyphenylmagnesium bromide prepared from 18.7 g (0.10 mol) of 2-bromoanisole and 2.43 g (0.10 mol) of magnesium turnings in ether under dry nitrogen was added 1.6 g (5.0 mmol) of 5-amino-4-cyano-3-methylthio-1-(2,4,6-trichlorophenyl)pyrazole and the resulting mixture was stirred and refluxed for 16 hours.

Upon cooling, the reaction was decomposed with 50 mL of saturated ammonium chloride solution. The organic phase was extracted with aqueous hydrogen chloride and the acidic extract was treated with 10 mL of concentrated hydrogen chloride and heated at 80–90° C. for 10 minutes after which the mixture was cooled and made alkaline. Extraction with methylene dichloride and chromatography of the extracts with mixtures of hexane and ethyl acetate gave 313 mg (14%) of the title compound, m.p. 200–202° C. Anal. Calcd. for $C_{18}H_{14}O_2N_3SCl_3$: C, 48.82; H, 3.18; N, 9.49. Found: C, 48.54; H, 3.32; N, 9.09.

EXAMPLE 4

A. 5-Amino-3-methyl-1-(2,4,6-trichlorophenyl)pyrazole

To a solution of 0.51 g (22.0 mmol) of sodium in methanol was added 1.66 g (20.0 mmol) of 5-methylisoxazole. The reaction mixture as refluxed for 8 hours and then stirred overnight at room temperature. Then 4.23 g (20.0 mmol) of 2,4,6-trichlorophenylhydrazine was added and the reaction mixture was again refluxed for 4 hours. A second portion of sodium In methanol was added and reflux was continued for 24 hours. The reaction mixture was taken up with ether and dilute hydrogen chloride. The organic extracts were washed with dilute hydrogen chloride and brine, and then dried with magnesium sulfate and evaporated to give crystals, m.p. 132–134° C. Analysis of this material, particularly two CN bands in the IR spectrum at 2190 $cm^{-1}$ and 2250 $cm^{-1}$, revealed it to be a mixture of the cis- and trans-isomers of 1-cyanoacetone-2,4,6-trichlorophenylhydrazone. This material was suspended in methanol and treated with 10.0 mmol of sodium methoxide in 5 mL of methanol. After 5 minutes at room temperature, water was added to crystallize the product which was filtered off and washed well with water. After air drying, the product weighed 2.21 g (40%) and melted at 134.0–135.5° C. Despite the similarity in melting points, the latter material was distinctly different from the former, having an $R_1$ of 0.67 vs. 0.78 for the intermediate on silica gel TLC plates developed with 1:1 hexane ethyl acetate and a distinctly different 300 MHz proton NMR spectrum.

B. 5-(2–Chlorobenzamido)-4-(2-chlorobenzoyl)-3-methyl-1-(2,4,6-trichlorophenyl)pyrazole A suspension of 2.34 g (17.50 mmol) of aluminum trichloride in 20 mL of 1,1,2,2-tetrachloroethane was treated with 2.02 mL (2.78 g, 15.9 mmol) of 2-chlorobenzoyl chloride and the resulting solution was stirred for 20 minutes at room temperature. Then 2.00 g (7.23 mmol) of the product of Step A was added and the reaction mixture was refluxed for 16 hours. The cooled reaction mixture was poured over ice and the insolubles were filtered off and washed with ethyl acetate. The organic layer was separated and the aqueous was washed twice with ethyl acetate. The combined organic layers were dried over magnesium sulfate and evaporated. The residues were chromatographed on silica gel, eluting with 4:1 hexane ethyl acetate to give 2.05 g (51%) of the title product, an amorphous foam. Anal. Calcd. for $C_{24}H_{14}O_2N_3Cl_5$: C, 52.06: H, 2.55; N, 7.59. Found: C, 52.11; H, 2.57; N, 7.27.

C. 5-Amino-4(2-chlorobenzoyl)-3-methyl-1-(2,4,6-trichlorophenyl)pyrazole

A solution of 1.94 g (3.50 mmol of the product of Step B in 20 mL of glacial acetic acid was treated with 20 mL of 48% hydrogen bromide and stirred at reflux for 8 hours. The cooled reaction mixture was treated with water to crystallize the product which was separated by filtration, washed with water and air dried to give the title product, 1.45 g (100%), m.p. softens about 210° C. and melts at 220° C. Anal. Calcd. for $C_{17}H_{11}ON_3Cl_4$: 412.9656. Found: 412.9722.

EXAMPLE 5

5-Methylamino4-(2-chlorobenzoyl)-3-methyl-1-(2,4,6-trichlorophenyl)pyrazole and 5-dimethylamino-4-(2-chlorobenzoyl)-3-methyl-1-(2,4,6-trichlorophenyl)pyrazole A solution of 0.208 g (0.5 mmol) of the compound of Example 4C in 20 mL of tetrahydrofuran (THF) was stirred in an ice/water bath while 5.0 mL of 1.0 M sodium hexamethyldisilazide in THF was added followed by 0.5 mL (1.14 g, 8 mmol) of methyl iodide. The reaction mixture was then stirred overnight at room temperature. The reaction mixture was poured into water and the products were extracted into ethyl acetate, dried and concentrated. The residues were chromatographed on silica gel using 5:1 hexane/ethyl acetate as eluent to give the less polar dimethylamino title compound, 52 mg (23%), m.p. 108–109° C. (ether/pentane).

The more polar product likewise crystallized from ether/pentane to give 39 mg (18%) of the monomethylamino title compound, m.p. 174–175° C.

EXAMPLE 6

5-amino-1 -(2,6-dichloro-4-trifluoromethylphenyl)-4-(2,5-dimethylbenzoyl)-3-(n-propyl)pyrazole A solution of 0.52 g (3.0 mmol) of 2,5-dimethylbenzoylacetonitrile, 0.45 g (3.0 mmol) of trimethylorthobutyrate and 0.632 g (0.58 mL, 6.2 mmol) of acetic anhydride in 5.0 mL of ethyl acetate was refluxed overnight and then cooled. The solvents were removed in vacuo and the residues were dissolved in 10 mL of ethanol. One-half of this solution, containing 1.5 mmol of 1 -cyano-1 -(2,5-dimethylbenzoyl)-3-methoxy-1-pentene was mixed with 0.7 mL (0.51 g, 5.0 mmol) of triethylamine and 0.37 g (1.50 mmol) of 2,6-dichloro-4-trifluoromethylphenylhydrazine and refluxed for 2.5 hours. The reaction mixture was cooled and partitioned between dilute hydrogen chloride and ethyl acetate. The organic phase was washed with water and then dried with brine and with magnesium sulfate. The solvent was evaporated to give an oil which was chromatographed on silica gel by the flash method eluting with 4:1 hexane/ethyl acetate to give the title compound as an amorphous foam. Anal. Calcd. for $C_{22}H_{20}ON_3Cl_2F_3$, 469.0935. Found: 469.0889.

EXAMPLE 7

A. 5-Amino-3-hydroxy-1-(2,4,6-trichlorophenyl)-pyrazole

Cyanoacetic acid (8.5 g, 0.10 mol) in 200 mL of dry ether was treated with 20.8 g (0.10 mol) of phosphorous pentachloride, warmed briefly to reflux and let cool to room temperature at which time all of the phosphorous pentachloride, had dissolved. After a small amount of insoluble material was removed by filtration, the ether was removed on the rotary evaporator. Then 100 mL of toluene was added and stripped to remove phosphorous oxytrichloride. The residual pale yellow oil was immediately dissolved in 50 mL of cold methylene dichloride and added to a cold suspension of 21.15 g (0.10 mol) of 2,4,6-trichlorophenylhydrazine in 14.0 mL of triethylamine and 100 mL of methylene dichloride, keeping the temperature below 20° C. by use of an ice bath. The reaction mixture was allowed to warm to room temperature and stirred for one hour. Then 500 mL of cold water was added. The precipitated solid was filtered and washed with water and with a little methylene dichloride to give the intermediate 2-cyano-N-(2,4,6-trichlorophenyl)acethydrazide, 14.92 g (54%), m.p. 166–168° C. Anal. Calcd. for $C_9H_6ON_3$: C, 38.81; H, 2.17; N, 15.09. Found: C, 38.83; H, 2.06; N, 14.81.

This material (14.92 g, 53 mmol) was dissolved in a solution of 2.80 g (0.12 mol) of sodium in 200 mL of methanol and refluxed for 4 hours. After stirring overnight at room temperature, the methanol was mostly evaporated and the residues were poured into water. The aqueous layer was extracted with ether and was then acidified with concentrated hydrogen chloride. The product was extracted into ethyl acetate. The extracts were dried with brine and magnesium sulfate and evaporated to give a foam which crystallized from ether to give 12.28 g (93%) of the title product, m.p. 221–223° C. Anal. Calcd. for $C_9H_6ON_3$: C, 38.81; H, 2.17; N, 15.09. Found: C, 38.81; H, 2.16; N, 14.84.

B. 3-Hydroxy-5-phthalimido-1-(2,4,6-trichlorophenyl) pyrazole

A mixture of 4.50 g (18.0 mmol) of the compound of Step A and 2.81 g (19.0 mmol) of phthalic anhydride in 40 mL of glacial acetic acid was refluxed for 4 hours and stirred overnight at room temperature. About two volumes of water were added dropwise and the resulting solid was filtered and washed with water. The damp solid was taken up in a little ethanol, filtered and washed with a little ethanol and ether, and air dried to give the title compound, 5.11 g (69%), m.p. 295–298° C.(dec). Anal. Calcd. for $C_{17}H_8O_3N_3Cl_3$: C, 49.97; H, 1.97; N. 10.28. Found: C, 49.28; H, 1.95; N, 10.06.

C. 4-(2–Chlorobenzoyl)-3-hydroxy-5-phthalimido-1-(2,4,6-trichlorophenylpyrazole

Aluminum trichloride (2.34 g, 17.6 mmol) was added to a solution of 2-chlorobenzoyl chloride in 60 mL of 1,1,2,2-tetrachloroethane and the resulting mixture was stirred for 30 minutes at room temperature. Then 2.87 g of the compound of Step B was added all at once and the reaction mixture was refluxed overnight. The cooled mixture was poured into water and the aqueous phase was extracted three times with ethyl acetate. The organic extracts were dried with brine and magnesium sulfate and evaporated to give a red oil which was taken up in methanol and crystallized to give the title compound, 2.97 g (77%), m.p. 245–246° C.

D. 4-(2-Chlorobenzoyl)-3-ethoxy-5-phthalimido-1-(2,4,6-trichlorophenyl)pyrazole

A solution of 0.55 g (1.0 mmol) of the compound of Step C in 10 mL of dry dimethyl sulfoxide was treated portionwise with 36 mg (1.5 mmol) of sodium hydride and the resulting mixture was stirred for 30 minutes at room temperature. Then 0.21 mL (0.25 g, 1.61 mmol) of diethyl sulfate was added and the reaction mixture was stirred for one hour at room temperature. The reaction mixture was poured into water and the product was extracted into ethyl acetate. The extracts were washed with water and dried with brine and magnesium sulfate, and evaporated to a gum. The product was crystallized from boiling ethanol to give the product (230 mg, 40%) as fine crystals, m.p. 215–216° C.

E. 5-Amino-4-(2-chlorobenzoyl)-3-ethoxy-1-(2,4,6-trichlorophenyl)pyrazole

A suspension of 184 mg of the compound of Step D in 10 mL of ethanol was treated with 0.5 mL of 55% hydrazine hydrate and refluxed for 1 hour. Solids in the cooled reaction mixture were filtered off and discarded and the filtrate was evaporated to a gum which was triturated with ether and filtered. The filtrate was again evaporated to a foam which was shown to be 104 mg of the analytically pure title compound. Anal. Calcd. for $C_{18}H_{13}O_2N_3Cl_4$: C, 48.57; H, 2.94; N, 9.44. Found, C, 48.41; H, 2.52; N, 9.43.

EXAMPLE 8

5-Dimethylamino-4-(2-chlorobenzoyl)-3-methoxy-1 (2,4,6-trichlorophenyl)pyrazole

A solution of 60 mg (0.14 mmol) of 5-amino-4-(2-chlorobenzoyl)methoxy-1-(2,4,6-trichlorophenyl) pyrazole prepared according to Example 7 in 5 mL of dry dimethyl sulfoxide was treated with 22 mg (0.88 mmol) of oil-free sodium hydride to give a yellow solution. After 1 hour at room temperature, 0.2 mL (0.46 g, 3.21 mmol) of methyl iodide was added. After stirring for 5 hours, the reaction mixture was poured into water and the product was extracted into ethyl acetate. After drying with brine and magnesium sulfate, the solvent was removed to give the title product as a one-spot foam. $^1$H-NMR (CDCl$_3$): 2.77 (6H, s), 3.63 (3H, s), 7.24–7.42 (4H, m), 7.48 (2H, s).

EXAMPLE 9

A. 3,3-Bis-ethoxy-2-(3-trifluoromethylbenzoyl)-acrylonitrile

Sodium (0.126 g, 5.5 mmol) was dissolved in 15 mL of ethanol and 20 mL of dioxane was added followed by 1.59 g (5.0 mmol) of 3,3-bis-methylthio-2-(3-trifluoromethylbenzoyl)-acrylonitrile and the reaction mixture was refluxed for 4 hours and let stir overnight at room temperature. This compound was relatively unstable to aqueous conditions and was not isolated as such. Instead, an aliquot of the mixture was stripped and the product was identified by 300 MHz proton NMR: NMR (DMSO d$_6$): 1.14 (6H, tJ=7), 3.45 (4H, q, J=7), 7.44–8.16 (4H, m).

B. 5-Amino-1-(2,6-dichloro-4-trifluoromethylphenyl)-3-ethoxy-4-(3-trifluoromethylbenzoyl)pyrazole An aliquot of the above solution of step A containing approximately two millimoles of 3,3-bis ethoxy-2-(3-trifluoromethylbenzoyl)acrylonitrile was reacted with 0.49 g (2.0 mmol) of 2,6-dichloro-4-trifluoromethylphenylhydrazine in 10 mL of ethanol under reflux overnight. The cooled mixture was poured into dilute hydrogen chloride (HCl) and the product was extracted into ethyl acetate (EtOAc), washed with water and brine, and dried over magnesium sulfate (MgSO$_4$). Chromatography on silica gel with 4:1 hexane/EtOAc gave the title product, 320 mg (31%), m.p. 77–78° C. from pentane.

EXAMPLE 10

5-Amino-1-(2 6-dichloro-4-trifluoromethylphenyl)-4-(2,5-dimethylbenzoyl)-3-ethoxypyrazole A solution of 0.26 g (1.5 mmol) of 2,5-dimethylbenzoylacetonitrile, 0.34 mL (0.31 g. 1.60 mmol) of tetraethylorthocarbonate and 0.30 mL (0.33 g, 3.20 mmol) of acetic anhydride in 10 mL of EtOAc was refluxed overnight. The solvent was evaporated and 10 mL of absolute ethanol was added and then stripped. The residues were dissolved in 10 mL of ethanol, 368 mg (1.5 mmol) of 2,6-dichloro-trifluoromethylphenyl-hydrazine and 0.7 mL (0.51 g, 5.0 mmol) of triethylamine were added, and the mixture was refluxed for 90 minutes. The mixture was poured into water, extracted with EtOAc and the organic extracts were washed with dilute HCl and brine, and dried over MgSO$_4$. Evaporation gave a gum which was chromatographed on silica gel with 4:1 hexane/EtOAc to give the title product which crystallized from pentane, 15 mg (2%), m.p. 99–101° C.

EXAMPLE 11

1-(2,6-Dichloro-4-trifluoromethylphenyl)-5-methyl-4-(3-methylbenzoyl)-3-methylthiopyrazole A solution of 2.97 g (16.9 mmol) of 4-(3-methylphenyl) butane-2,4-dione and 4.04 mL (5.14 g, 67.6 mmol) of carbon disulfide in 60 mL of dry dimethyl sulfoxide was treated portionwise with 0.89 g (37.1 mmol) of oil-free sodium hydride at 15–18° C. After stirring 30 minutes, 2.31 mL (5.27 g, 37.1 mmol) of methyl iodide was added dropwise and the reaction mixture was allowed to stir at room temperature for 1 hour. It was then poured into water and the product was extracted into ether, backwashed with water and dried over MgSO$_4$ to give 4.30 g (91%) of an oil which crystallized in the refrigerator overnight, m.p. 44–46° C. $^1$H-NMR (CDCl$_3$): 2.16 (3H, s), 2.38 (6H, s), 2.72 (3H, s), 7.26–7.38 (2H, m), 7.58–7.74 (2H, m). A mixture of 1.95 g (6.96 mmol) of 3,3-bismethylthio-2-(3-methylbenzoyl)-2-acetylethene and 1.71 g of 2,6-dichloro-4-trifluoromethylphenylhydrazine in 20 mL of ethanol was refluxed for 6 hours and then stirred at room temperature for 48 hours. The reaction mixture was poured into dilute HCl solution and the product was extracted into EtOAc. The solution was dried and concentrated and the residues were chromatographed on silica gel with 10:1 hexane/EtOAc to give the title product which crystallized from pentane, 1.67 g (52%), m.p. 103–104° C.

EXAMPLE 12

5-Amino-1-(2,6-dichloro-4-trifluoromethylphenyl)-4-(5-[3-hydroxypropyl]-2-methylbenzoyl)-3-methylthiopyrazole A solution of 0.530 g (1.0 mmol) of 5-amino-1-(2,6-dichloro-4-trifluoromethylphenyl)-4-(5-[β-methoxycarbonylethyl]-2-methylbenzoyl)-3-methylthiopyrazole in 10 mL of THF was cooled in an ice bath while 1.33 mL of a 1.5 M solution of DIBAL in THF was added. The reaction mixture was warmed to room temperature and then quenched with water. The product was extracted into EtOAc, dried and concentrated. The residues were chromatographed on silica gel using mixtures of hexane/EtOAc to elute the title product which was isolated as an amorphous foam, 174 mg (34%). Anal. Calcd. for C$_{22}$H$_{20}$O$_2$N$_3$SCl$_2$F$_3$: C, 50.97; H, 3.88; N, 8.10. Found, C, 51.10; H, 3.96; N, 7.60.

EXAMPLE 13

[5-Amino-1-(2,6-dichloro-4-trifluoromethylphenyl)-3-methylsulfonyl-1H-pyrazol-4-yl]-(2,5-dimethylphenyl)methanone To a solution of 200 mg (0.42 mmol) of [5-amino-1-(2,6-dichloro-4-trifluoromethylphenyl)-3-methylsulfanyl-1H-pyrazol-4-yl]-(2,5-dimethylphenyl)methanone in 10 mL of THF was added 0.176 g (2.10 mmol) of anhydrous sodium bicarbonate followed by a solution of 145 mg (0.42 mmol) of 3-chloroperoxybenzoic acid in 8 mL of THF. After two hours at room temperature, 0.5 g of sodium bicarbonate and an additional 290 mg (0.84 mmol) of 3-chloroperoxybenzoic acid was added. The reaction mixture was heated briefly to 50° C., let cool and stirred overnight at room temperature. The reaction mixture was added to water and the product was extracted into ethyl acetate. The organic extracts were washed with dilute sodium bicarbonate solution and then dried and evaporated. The title compound was crystallized from ether to give 150 mg (70% yield) of colorless crystals, m.p. 193.5–194.5° C.

EXAMPLE 14

The following compounds in Tables 1 and 2 were prepared according to the indicated Example.

TABLE 1

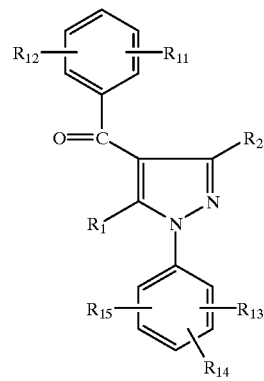

| R$_1$ | R$_2$ | R$_{13}$ | R$_{14}$ | R$_{15}$ | R$_{11}$ | R$_{12}$ | Physical Data (m.p. in ° C.) | Process of Example |
|---|---|---|---|---|---|---|---|---|
| amino | SCH$_3$ | 2-Cl | 4-Cl | 6-Cl | 2-Cl | H | m.p. 178–180 | 1 |
| amino | SCH$_3$ | 2-Cl | 4-Cl | 6-Cl | H | H | m.p. 178–180 | 1 |
| amino | SCH$_3$ | 4-CF$_3$ | H | H | 2-Cl | H | m.p. 150–153 | 1 |
| amino | SCH$_3$ | 2-Cl | 4-Cl | 6-Cl | 2-F | H | m.p. 204–206 | 1 |
| NHCH$_3$ | SCH$_3$ | 2-Cl | 4-Cl | 6-Cl | 2-Cl | H | m.p. 135–137 | 2 |
| N(CH$_3$)$_2$ | SCH$_3$ | 2-Cl | 4-Cl | 6-Cl | 2-Cl | H | m.p. 194–197 | 2 |
| N(CH$_3$)$_2$ | CH$_3$ | 2-Cl | 4-Cl | 6-Cl | 2-Cl | H | m.p. 220–222 | 6 |
| amino | SCH$_3$ | 2-CF$_3$ | H | H | 2-Cl | H | m.p. 186–188 | 1 |
| amino | SCH$_3$ | 2-Cl | 4-Cl | 6-Cl | 2-cyclopropyl | H | m.p. 165–167 | 1 |
| amino | SCH$_3$ | 2-Cl | 4-Cl | 6-Cl | 4-CH$_3$ | H | m.p. 230–232 | 1 |
| amino | SCH$_3$ | 2-Cl | 4-Cl | 6-Cl | 2-Cl | 4-Cl | m.p. Amorphous. Anal. Calc'd for C17H10N3OSCl5: C, 42.39; H, 2.09; N, 8.72. Found: C, 41.94; H, 2.06; N, 8.07. | 1 |
| N(CH$_3$)$_2$ | CH$_3$ | 2-Cl | 4-Cl | 6-Cl | 2-Cl | H | m.p. 108–109 | 6 |
| NH$_2$ | SCH$_3$ | 2-F | 4-F | 6-F | 2-Cl | H | m.p. 156–158 | 1 |
| N(CH$_3$)$_2$ | SCH$_3$ | 2-Cl | 4-Cl | 6-Cl | 2-F | H | m.p. Amorphous. | 2 |

-continued

| $R_1$ | $R_2$ | $R_{13}$ | $R_{14}$ | $R_{15}$ | $R_{11}$ | $R_{12}$ | Physical Data (m.p. in ° C.) | Process of Example |
|---|---|---|---|---|---|---|---|---|
| | | | | | | | HRMS for C19H15N3OSCl3F Calc'd: 456.9984 Found: 456.9990 | |
| $NH_2$ | $SCH_3$ | 2-Cl | 6-Cl | H | 2-F | H | m.p. 182–184 | 1 |
| $NH_2$ | $SCH_3$ | 2-F | 4-F | H | 2-Cl | H | m.p. 147–150 | 1 |
| $N(CH_3)_2$ | $SCH_3$ | 2-Cl | 4-Cl | 6-Cl | 3-Cl | H | m.p. 121–125 | 2 |
| $NH_2$ | $NHCH_3$ | 2-Cl | 4-Cl | 6-Cl | 2-Cl | H | m.p. 86–90 | |
| $NH_2$ | $SCH_3$ | 2-Cl | 4-Cl | 6-Cl | 2-$OCH_3$ | H | m.p. 200–202 | 1 |
| $NH_2$ | $SCH_3$ | 2-Cl | 6-Cl | 4-$CF_3$ | 2-Cl | H | m.p. 207–210 | 1 |
| $NH(CH_2)_3OC_6H_5$ | $SCH_3$ | 2-Cl | 6-Cl | 4-Cl | 2-Cl | H | m.p. Amorphous. Anal. Calcd. for C26H21N3O2SCl4: C, 53.71; H, 3.64; N, 7.22. Found: C, 53.57; H, 3.41; N, 7.46. | 5 |
| $NH_2$ | $SCH_3$ | 2-Cl | 6-Cl | 4-Cl | 3-$CH_3$ | H | m.p. 178–180 | 1 |
| $NH_2$ | $SCH_3$ | 2-Cl | 6-Cl | 4-$CF_3$ | 3-Cl | H | m.p. 149–151 | 1 |
| $NH_2$ | $SCH_3$ | 2-Cl | 6-Cl | 4-$CF_3$ | 3-$CH_3$ | H | m.p. 150–153 | 1 |
| $N(CH_3)_2$ | $SCH_3$ | 2-Cl | 6-Cl | 4-$CF_3$ | 3-Cl | H | m.p. 120–122 | 2 |
| $NH_2$ | $SCH_3$ | 2-Cl | 6-Cl | 4-Cl | 3-$CF_3$ | H | m.p. 158–160 | 1 |
| $NHCH_2COOH$ | $SCH_3$ | 2-Cl | 6-Cl | 4-Cl | 2-Cl | H | m.p. > 250 HRMS for $C_{19}H_{13}N_3O_3SCl_4$: Calcd: 525.9930 Found: 525.9348 | 1 |
| $NH_2$ | $SCH_3$ | 2-Cl | 6-$CF_3$ | 4-Cl | 3-$CF_3$ | H | m.p. Amorphous. Anal. Calcd. for C19H11N3OSCl2F6: C, 44.30; H, 2.16; N, 8.15. Found: C, 44.51; H, 2.29; N, 7.98 | 1 |
| $NH_2$ | $SCH_3$ | 2-$CH_3$ | 4-Cl | H | 2-Cl | H | m.p. 125–129 | 1 |
| $NH_2$ | $SCH_3$ | 2-$CH_3$ | 4-Cl | H | 3-Cl | H | m.p. 112–115 | 1 |
| $NH_2$ | $SCH_3$ | 2-Cl | 4-$CF_3$ | 6-Cl | 2-$CH_3$ | 5-$CH_3$ | m.p. 130–132 | 1 |
| $NH_2$ | $SCH_3$ | 2-$CH_3$ | 6-$CH_3$ | H | 3-Cl | H | m.p. 148–151 | 1 |
| $N(CH_3)_2$ | $SCH_3$ | 2-Cl | 4-$CF_3$ | 6-Cl | 3-$CF_3$ | H | m.p. Amorphous. Anal. Calcd. for C21H15N3OSCl2F6: C, 46.50; H, 2.78; N, 7.74. Found: C, 46.75; H, 2.93; N 7.58 | 2 |
| $NH_2$ | $SCH_3$ | 2-Cl | 4-$CF_3$ | H | 3-Cl | H | m.p. 124–127 | |
| $NH_2$ | $SCH_3$ | 2-$CH_3$ | 6-$CH_3$ | H | 3-Cl | H | m.p. 139–142 | 1 |
| $NH_2$ | $SCH_3$ | 2-Cl | 4-Cl | 6-Cl | 2-$CH_3$ | 5-$CH_3$ | m.p. 182–184 | 1 |
| $CH_3$ | $SCH_3$ | 2-Cl | 4-Cl | 6-Cl | 3-$CH_3$ | H | m.p. 116–117 | |
| $NH_2$ | $SCH_3$ | 2-$CH_3$ | 4-Cl | 6-$CH_3$ | 3-$CF_3$ | H | m.p. Amorphous. Anal. Calcd. for C20H17N3OSClF3: C, 54.48; H, 3.88; N, 9.53. Found: C, 54.60; H, 3.91; N, 9.08 | 1 |
| $NH_2$ | $SCH_3$ | 2-$CH_3$ | 4-Cl | 6-$CH_3$ | 3-Cl | H | m.p. Amorphous. Anal. Calcd. for C19H17N3OSCl2: C, 56.16; H, 4.21; N, 10.34. Found: C, 55.93; H, 4.21; N, 10.01 | 1 |
| $NH_2$ | $SCH_3$ | 2-$CH_3$ | 4-$CH_3$ | 6-$CH_3$ | 3-Cl | H | m.p. 163–165 | 1 |
| $NH_2$ | $SCH_3$ | 2-$CH_3$ | 4-$CH_3$ | 6-$CH_3$ | 3-$CH_3$ | H | m.p. 124–127 | 1 |
| $NH_2$ | $SCH_3$ | 2-$CH_3$ | 4-$CH_3$ | 6-$CH_3$ | 3-$CF_3$ | H | m.p. 143–146 | 1 |
| $NH_2$ | $SCH_3$ | 2-$CH_3$ | 4-Br | 6-$CH_3$ | 3-$CF_3$ | H | m.p. Amorphous. Anal. Calcd. for C20H17N3OSBrF3: C, 49.59; H, 3.53; N, 8.67. Found: C, 49.45; H, 3.49; N, 8.37 | 1 |
| $NH_2$ | $SCH_3$ | 2-Cl | 4-$CF_3$ | 6-Cl | 2-$CH_3$ | 3-$CH_3$ | m.p. 196–198 | 1 |
| $NH_2$ | $SCH_3$ | 2-$CH_3$ | 4-Br | 6-$CH_3$ | 3-Cl | H | m.p. Amorphous. Anal. Calcd. for | 1 |

-continued

| $R_1$ | $R_2$ | $R_{13}$ | $R_{14}$ | $R_{15}$ | $R_{11}$ | $R_{12}$ | Physical Data (m.p. in °C.) | Process of Example |
|---|---|---|---|---|---|---|---|---|
| | | | | | | | C19H17N3OSBrCl: C, 50.63; H, 3.80; N, 9.32. Found: C, 50.40; H, 3.77; N, 8.94 | |
| $NH_2$ | $SCH_3$ | 2-Cl | 4-$CF_3$ | 6-Cl | 2-$CH_3$ | 5-$(CH_2)_3$—$CO_2CH_3$ | m.p. Amorphous. Anal. Calcd. for C24H22N3O3SCl2F3: C, 51.43; H, 3.96; N, 7.50. Found: C, 51.59; H, 4.10; N, 7.17 | 1 |
| $NH_2$ | $SCH_3$ | 2-$CH_3$ | 6-$CH_3$ | 4-Br | 2-$CH_3$ | 5-$CH_3$ | m.p. Amorphous. Anal. Calcd. for $C_{21}H_{22}N_3OS$: C, 56.76; H, 4.99; N, 9.45. Found: C, 56.37; H, 5.01; N, 9.04 | 1 |
| $NH_2$ | $SCH_3$ | 2-Cl | 4-$CF_3$ | 6-Cl | 2-$OCH_3$ | H | m.p. 172–174 | 1 |
| $NH_2$ | $OCH_3$ | 2-Cl | 4-Cl | 6-Cl | 2-Cl | H | m.p. Amorphous. $^1$H-NMR($CDCl_3$):3.68 (3H, s), 5.86(2H, broad s), 7.26–7.44(4H, m)7.51(2H, s). | 7 |
| $NH_2$ | $OCH_2CH_3$ | 2-Cl | 4-Cl | 6-Cl | 2-Cl | H | m.p. Amorphous. Anal. Calcd. for C18H13N3O2Cl4: C, 48.57; H, 2.94; N, 9.44. Found: C, 48.41; H, 2.52; N, 9.43 | 7 |
| $N(CH_3)_2$ | $OCH_3$ | 2-Cl | 4-Cl | 6-Cl | 2-Cl | H | m.p. Amorphous. HRMS for C19H15N3O2Cl4: Calcd: 456.9913 Found: 456.9960 | 8 |
| $NH_2$ | $OCH_2CH_3$ | 2-Cl | 4-$CF_3$ | 6-Cl | 3-$CF_3$ | 5-$CF_3$ | m.p. Amorphous. Anal. Calcd. for C20H10N3OSCl2F9: C, 41.25; H, 1.73; N, 7.21. Found: C, 41.49; H, 2.01; N, 7.01 | 1 |
| $NH_2$ | $OCH_2CH_3$ | 2-Cl | 4-$CF_3$ | 6-Cl | 2-$CH_3$ | 5-$CH_3$ | m.p. Amorphous. High Resolution Mass Spectrum Calcd. for C22H20N3OCl2F3: 472.0806. Found, 472.0817 | 1 |
| $NH_2$ | $CH_2CH_2$—$CH_3$ | 2-Cl | 4-$CF_3$ | 6-Cl | 2-$CH_3$ | 5-$CH_3$ | m.p. Amorphous. High Resolution Mass Spectrum Calcd. for $C_{21}H_{20}N_3OC_{12}F_3$: 469.0935. Found: 469.0889 | 6 |
| $NH_2$ | $CH_2CH_2$—$CH_3$ | 2-Cl | 4-Cl | 6-Cl | 2-$CH_3$ | 5-$CH_3$ | m.p. Amorphous. High Resolution Mass Spectrum Calcd. for C22H20N3OCl2F3: 436.0761. Found: 436.0764 | 6 |
| $NH_2$ | $SCH_3$ | 2-Cl | 4-$CF_3$ | 6-Cl | 3-$OCH_3$ | H | m.p. Amorphous. $^1$H-NMR($CDCl_3$)δ 2.38(3H, s), 3.90(3H, s), 5.79(2H, broad s), 7.07(1H, d, J=7), 7.16(1H, s), 7.23(1H, d, J=7), 7.39(1H, t, J=7), 7.79(2H, s) | 3 |
| $NH_2$ | $SCH_3$ | 2-Cl | 4-$CF_3$ | 6-Cl | 2-$CH_3$ | 5-$(CH_2)_4OH$ | m.p. Amorphous. High Resolution | 12 |

-continued

| R₁ | R₂ | R₁₃ | R₁₄ | R₁₅ | R₁₁ | R₁₂ | Physical Data (m.p. in °C.) | Process of Example |
|---|---|---|---|---|---|---|---|---|
| NH₂ | CH₂CH₃ | 2-Cl | 4-CF₃ | 6-Cl | 2-CH₃ | 5-CH₃ | Mass Spectrum Calcd. for C23H22N3O2SCl2F3: 532.0840. Found: 532.0871 m.p. Amorphous. Anal. Calcd. for C21H18N3OCl2F3: C, 55.29; H, 3.97; N, 8.21. Found: C, 55.62; H, 4.35; N, 8.15 | 6 |
| NH₂ | CH₂CH₃ | 2-Cl | 4-Cl | 6-Cl | 2-CH₃ | 5-CH₃ | m.p. Amorphous. Anal. Calcd. for C20H18N3OCl3: C, 56.81; H, 4.29; N, 9.94. Found: C 56.88; H, 4.09; N, 9.62 | 6 |
| NH₂ | SCH₃ | 2-Cl | 4-CF₃ | 6-Cl | 2-CF₃ | 5-CF₃ | m.p. Amorphous. Anal. Calcd. for C20H20N3OSCl2F9: C, 41.25; H, 1.71; N, 7.21. Found: C, 41.20; H, 1.87; N, 6.89 | 1 |
| NH₂ | SCH₃ | 2-Cl | 4-CF₃ | 6-Cl | 2-CH₃ | 5-CH₂CO₂—C₂H₅ | m.p. Amorphous. Anal. Calcd. for C23H20N3O3SCl2F3: C, 50.55; H, 3.68; N, 7.69. Found: C, 50.50; H, 3.50; N, 7.29 | 1 |
| NH₂ | SCH₃ | 2-Cl | 4-CF₃ | 6-Cl | 2-CH₃ | 5-(CH₂)₂OH | m.p. Amorphous. HRMS for C21H18N3O2SCl2F3 Calcd: 503.0646 Found: 503.0147 | 12 |
| NH₂ | SCH₃ | 2-Cl | 4-CF₃ | 6-Cl | 2-OCH₃ | 5-OCH₃ | m.p. Amorphous. ¹H-NMR(CDCl₃)δ 2.30(3H, s), 3.60(6H, s), 5.85(2H, broad s), 6.80–6.96(3H, m), 7.74(2H, s). | 1 |
| NH₂ | OCH₂CH₃ | 2-Cl | 4-CF₃ | 6-Cl | 3-CF₃ | H | m.p. 112–114 | 9 |
| NH₂ | OCH₂CH₃ | 2-Cl | 4-CF₃ | 6-Cl | 3-CF₃ | H | m.p. 77–78 | 9 |
| NH₂ | OCH₂CH₃ | 2-Cl | 4-CF₃ | 6-Cl | 3-CH₃ | H | m.p. 103–104 | 9 |
| NH₂ | OCH₂CH₃ | 2-CH₃ | 4-Br | 6-CH₃ | 3-CF₃ | H | m.p. 158–160 | 9 |
| NH₂ | SCH₃ | 2-Cl | 4-CF₃ | 6-Cl | 2-CH₃ | 5-isopropyl | m.p. Amorphous. Anal. Calcd. for C22H20N3OSCl2F3: C, 52.59; H, 3.98; N, 8.36. Found: C, 52.39; H, 4.01; N, 8.08 | 1 |
| NH₂ | SCH₃ | 2-Cl | 4-CF₃ | 6-Cl | 2-CH₃ | 5-(CH₂)₃OH | m.p. Amorphous. Anal. Calcd. for C22H20N3O2SCl2F3: C, 50.97; H, 3.88; N, 8.10. Found: C, 51.10; H, 3.96; N, 7.60 | 12 |
| NH₂ | SCH₃ | 2-Cl | 4-CF₃ | 6-Cl | 2-COOC₂H₅ | H | m.p. 211–216 | 1 |
| NH₂ | SCH₃ | 2-Cl | 4-CF₃ | 6-Cl | R₁₁ and R₁₂ with the phenyl to which they are attached form 1-naphthyl | H | m.p. 115–118 | 1 |
| NH₂ | SCH₃ | 2-Cl | 4-CF₃ | 6-Cl | 3-Br | H | m.p. Amorphous. Calcd. for C18H11N3OSBrCl2F3 C 41.16, H 2.11, N 8.00. | 1 |

| $R_1$ | $R_2$ | $R_{13}$ | $R_{14}$ | $R_{15}$ | $R_{11}$ | $R_{12}$ | Physical Data (m.p. in ° C.) | Process of Example |
|---|---|---|---|---|---|---|---|---|
| $NH_2$ | $SCH_3$ | 2-Cl | 4-$SO_2$—$NH_2$ | 6-Cl | 3-$CF_3$ | H | Found C 41.37, H 1.92, N 7.85. m.p. 272–274 | 1 |
| $NH_2$ | $SCH_3$ | 2-Cl | 4-$CF_3$ | 6-Cl | 3-$SO_2NH_2$ | H | m.p. 99–100 | 1 |
| $NH_2$ | $SCH_3$ | 2-$CH_3$ | 4-Br | 6-$CH_3$ | 3-$SO_2NH_2$ | H | m.p. 242–244 | 1 |
| $NH_2$ | $SCH_3$ | 2-Cl | 4-$CF_3$ | 6-Cl | 3-$SO_2N(CH_3)_2$ | H | m.p. Amorphous. Anal. Calcd. for C20H17N4O3S2Cl2F3/1/4C4H10O: C, 44.10; H, 3.44; N, 9.80. Found: C, 43.88; H, 3.29; N, 9.68 | 1 |
| $NH_2$ | $SCH_3$ | 2-$CH_3$ | 4-Br | 6-$CH_3$ | 3-$SO_2N(CH_3)_2$ | H | m.p. Amorphous. Anal. Calcd. for C21H23N4O3S2Br: C, 48.18; H, 4.43; N, 10.70. Found: C, 48.42; H, 4.24; N, 10.52 | 1 |
| $NH_2$ | $SCH_3$ | 2-Cl | 4-$CF_3$ | 6-Cl | 3-$SO_2N(CH_3)_2$ | H | m.p. 192–194 | 1 |
| $NH_2$ | $SCH_3$ | 2-Cl | 4-Cl | 6-Cl | 2-(2-thienyl) | H | m.p. 171.5–172.5 | 1 |
| $NH_2$ | $SCH_3$ | 2-Cl | 6-Cl | 4-$CF_3$ | H | H | m.p. 192–194 | 1 |
| $NH_2$ | $CH_3$ | 2-Cl | 6-Cl | 4-$CF_3$ | 2-$CH_3$ | 5-$CH_3$ | m.p. 175–176 | 6 |
| $NH_2$ | $CH_3$ | 2-$CH_3$ | 6-$CH_3$ | 4-Br | 2-$CH_3$ | 5-$CH_3$ | m.p. 158–160 | 6 |
| $NH_2$ | $SCH_3$ | 2-Cl | 6-Cl | 4-$CF_3$ | 3-$N(CH_3)_2$ | H | HRMS for $C_{20}H_{17}ON_4SCl_2F_3$ Calcd: 488.0452 Found: 488.0408 | 1 |
| $NH(C_3H_7)$ | $SCH_3$ | 2-Cl | 6-Cl | 4-Cl | 2-Cl | H | Calcd. C, 49.10; H, 3.50; N, 8.54; Found: C, 50.37; H, 3.26; N, 8.47. | 5 |
| $NH_2$ | $SO_2CH_3$ | 2-Cl | 6-Cl | 4-$CF_3$ | 2-$CH_3$ | 5-$CH_3$ | m.p. 193.5–194.5 | 13 |
| $NH_2$ | $SCH_3$ | 2-Cl | 6-Cl | 4-$CF_3$ | 3-phenyl | H | m.p. 124–127 | 1 |
| $NH_2$ | $SCH_3$ | 2-Cl | 6-Cl | 4-$CF_3$ | 2-pyrrolyl | H | HRMS Calcd. 510.0295 Found 510.0455 | 1 |
| $N(CH_3)(C_2H_5)$ | $SCH_3$ | 2-Cl | 6-Cl | 4-Cl | 2-Cl | H | FAB Mass Spectrum: 490 | 5 |
| $NH_2$ | $SCH_3$ | 2-Cl | 6-Cl | 4-Cl | 2-$CH_3$ | 5-iPr | HRMS Calcd. 467.0393 Found 467.0395 | 1 |
| $NH_2$ | $SCH_3$ | 2-Cl | 6-Cl | 4-$CF_3$ | 2-$CH_3$ | 5-n-butyl | HRMS Calcd. 515.0809 Found 515.0892 | 1 |
| $N(C_2H_5)_2$ | $SCH_3$ | 2-Cl | 6-Cl | 4-$CF_3$ | 2-$CH_3$ | 5-iPr | HRMS Calcd. 557.1277 Found 557.1287 | 5 |
| $NH_2$ | $CH_3$ | 2-Cl | 6-Cl | 4-Cl | 2-$CH_3$ | 5-iPr | HRMS Calcd. 435.0669 Found 435.0682 | 1 |
| $N(C_2H_5)(C_3H_7)$ | $SCH_3$ | 2-Cl | 6-Cl | 4-$CF_3$ | 2-$CH_3$ | 5-iPr | MS parent 571, 529, 494, 360, 160 (100%) | 5 |
| $N(C_2H_5)$ (sec-butyl) | $SCH_3$ | 2-Cl | 6-Cl | 4-$CF_3$ | 2-$CH_3$ | 5-iPr | HRMS Calcd. 585.1589 Found 585.1500 | 5 |
| $N(CH_3)(C_2H_5)$ | $SCH_3$ | 2-Cl | 6-Cl | 4-$CF_3$ | 2-$CH_3$ | 5-iPr | HRMS Calcd. 543.1121 Found 543.1166 | 5 |
| $N(C_2H_5)(C_3H_7)$ | $SCH_3$ | 2-Cl | 6-Cl | 4-$CF_3$ | 2-$CH_3$ | 5-iPr | HRMS Calcd. 569.1277 Found 569.1433 | 5 |
| $NH_2$ | $SCH_3$ | 2-Cl | 6-Cl | 4-$CF_3$ | 2-n-propyl | 5-$CH_3$ | HRMS Calcd. 501.0653 Found 501.0551 | 1 |
| $NH_2$ | $SCH_3$ | 2-Cl | 6-Cl | 4-$CF_3$ | 2-$CH_3$ | 5-n-propyl | HRMS Calcd. 501.0653 Found 501.0698 | 1 |
| $N(CH_3)(C_2H_5)$ | $SCH_3$ | 2-Cl | 6-Cl | 4-$CF_3$ | 2-$CH_3$ | 5-iPr | HRMS Calcd. 555.1121 Found 555.0756 | 5 |
| $NH_2$ | $SCH_3$ | 2-Cl | 4-Cl | 6-Cl | 2-$CH_3$ | 6-$CH_3$ | HRMS Calcd. 439.0080 Found 439.0097 | 1 |

-continued

| R₁ | R₂ | R₁₃ | R₁₄ | R₁₅ | R₁₁ | R₁₂ | Physical Data (m.p. in ° C.) | Process of Example |
|---|---|---|---|---|---|---|---|---|
| $NH_2$ | $SCH_3$ | 2-Cl | 4-$CF_3$ | 6-Cl | 2-Cl | 6-Cl | m.p. 212–213 | 1 |
| $NH_2$ | $SCH_3$ | 2-$CH_3$ | 4-Br | 6-$CH_3$ | 2-Cl | 6-Cl | m.p. 252–254 | 1 |
| $NH_2$ | $SCH_3$ | 2-Cl | 4-Cl | 6-Cl | 2-Cl | 6-Cl | m.p. 237–239 | 1 |
| $NH_2$ | $SCH_3$ | 2-Cl | 4-Cl | 6-Cl | 2-$OCH_3$ | H | m.p. 168–171 | 1 |
| $NH_2$ | $SCH_3$ | 2-Cl | 4-$CF_3$ | 6-Cl | 2-OiPr | 5-Cl | MS 537 (parent ion) 480, 341(100%), 308, 255, 155 | 1 |
| $NH_2$ | $SCH_3$ | 2-$CH_3$ | 4-Br | 6-$CH_3$ | 2-$OCH_3$ | 5-Br | m.p. 191–193 | 1 |
| $NH_2$ | $SCH_3$ | 2-Cl | 4-$CF_3$ | 6-Cl | 2-$OCH_3$ | 5-Br | m.p. 192–194 | 1 |
| $NH_2$ | $SCH_3$ | 2-Cl | 4-Cl | 6-Cl | 2-$OCH_3$ | 5-Br | m.p. 218–220 | 1 |
| $NH_2$ | $SCH_3$ | 2-Cl | 4-Cl | 6-Cl | 2-Br | 5-Br | m.p. 229–231 | 1 |
| $NH_2$ | $SCH_3$ | 2-Cl | 4-$CF_3$ | 6-Cl | 2-Br | 5-Br | m.p. 172–174 | 1 |
| $NH_2$ | $SCH_3$ | 2-$CH_3$ | 4-Br | 6-$CH_3$ | 2-Br | 5-Br | m.p. 179–181 |  |
| $NH_2$ | $SCH_3$ | 2-$CH_3$ | 4-$CH_3$ | 6-$CH_3$ | 2-Br | 5-Br | m.p. 195–197 |  |
| $NH_2$ | $SCH_3$ | 2-$CH_3$ | 4-Br | 6-$CH_3$ | 2-$CH_3$ | 5-$NO_2$ | m.p. 118–119 | 1 |
| $NH_2$ | $SCH_3$ | 2-Cl | 4-Cl | 6-Cl | 2-$C_2H_5$ | H | m.p. 146–150 | 1 |
| $NH_2$ | $SCH_3$ | 2-Cl | 4-Cl | 6-Cl | 2-$CF_3$ | H | m.p. 175–177 | 1 |
| $NH_2$ | $SCH_3$ | 2-Cl | 4-$CF_3$ | 6-Cl | 2-Cl | 5-$NO_2$ | m.p. 98.0–98.5 | 1 |
| $NH_2$ | $SCH_3$ | 2-$CH_3$ | 4-Br | 6-$CH_3$ | 2-Cl | 5-$NO_2$ | m.p. 116–118 | 1 |
| $NH_2$ | $SCH_3$ | 2-Cl | 4-$CF_3$ | 6-Cl | 2-$CH_3$ | 5-$NO_2$ | m.p. 99–100 | 1 |
| $NH_2$ | $SCH_3$ | 2-$CH_3$ | 4-$CH_3$ | 6-$CH_3$ | 2-$CH_3$ | 5-$NO_2$ | m.p. 193–195 | 1 |
| $NH_2$ | $SCH_3$ | 2-Cl | 4-Cl | 6-Cl | 2-$OC_3H_7$ | H | $^1$H-NMR($CDCl_3$)δ 0.87(3H, t, J=7), 1.68(2H, m), 2.32(3H, s), 3.96(2H, q, J=7), 5.80(1H, broad s), 6.93(1H, d, J=7), 7.031H, t, J=7), 7.27(1H, d, J=7), 7.42(1H, t, J=7), 7.52(2H, s) | 1 |

TABLE 2

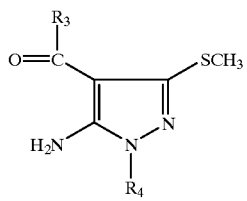

| R₃ | R₄ | Phys. Data (m.p. in ° C.) | Process of Example |
|---|---|---|---|
| $C_2H_5CHC_4H_9$ | 2,6-$Cl_2$-4-$CF_3$Ph | HRMS Calcd. 467.0809. Found 467.0913. | 1 |
| $C_3H_7CH=CH—C_2H_5$ | 2,6-$Cl_2$-4-$CF_3$Ph | FAB Mass Spectrum: 466 | 1 |
| 2-methylcyclopentyl | 2,4,6-$Cl_3$Ph | HRMS Calcd. 417.0236. Found 417.0328. | 1 |
| 2-$OC_2H_5$-1-naphthyl | 2,6-$Cl_2$-4-$CF_3$Ph | m.p. 149–151 | 1 |
| 2-$OC_2H_5$-1-naphthyl | 2,4,6-$Cl_3$Ph | m.p. 125–128 | 1 |
| 3-$CF_3$—Ph | 1,3-$(CH_3)_2$-4-$NO_2$—pyrazol-5-yl | Calcd. for $C_{17}H_{15}O_3N_6SF_3$: C, 46.36; H, 3.43; N, 19.08. Found: C, 46.51; H, 3.37; N, 18.10. | 1 |

EXAMPLE 15

A. 3-Trifluoromethylphenylthioacetonitrile

To sodium (0.62 g, 27.0 mmol) dissolved in 40 mL of ethanol was added 4.79 g (26.9 mmol) of 3-trifluoromethylthiophenol and 2.04 g (27.0 mmol) of chloroacetonitrile. The reaction mixture was heated at reflux for 1 hour and then stirred overnight at room temperature. To the cooled reaction mixture was added one volume of ether and the precipitated solids were removed by filtration. The filtrate was evaporated on the rotary evaporator to give the product as an oil in essentially quantitative yield. This material was used in the following reaction without further purification.

B. 3-Trifluoromethylphenylcyanomethylsulfoxide

A solution of 3.00 g (13.8 mmol) of 3-trifluoromethylphenylthioacetonitrile in 130 mL of methylene chloride was cooled to 5° C. under dry $N_2$ and treated with 4.89 g (28.35 mmol) of m-chloroperbenzoic acid. The reaction mixture was stirred for 48 hours at room temperature and then cooled in ice, after which the insolubles were removed by filtration. The filtrate was washed with 10% sodium sulfate solution until all traces of peroxides had been removed and then dried over magnesium sulfate and evaporated to a pale yellow oil which was used in the subsequent reaction without further purification.

C. 3,3-Bis-methylthio-2-(3-trifluoromethylphenylsulfonyl) acrylonitrile

A solution of 13.82 mmol (crude product) of 3-trifluoromethylphenylcyanomethylsulfoxide in 30 mL of dry dimethylsulfoxide and 1.25 mL (1.58 g, 20.7 mmol) of $CS_2$ was cooled to about 150° C. in an ice bath under dry nitrogen. Then 0.99 g (41.5 mmol) of oil-free sodium hydride was added portionwise below 20° C. and the deep red solution was let stir at room temperature for 75 minutes. The reaction mixture was cooled to 15° C., quenched with 2.58 mL (5.89 g, 41.5 mmol) of methyl iodide and let stir overnight at room temperature. The reaction mixture was poured into ice/water and let granulate for 3.5 hours. The product was filtered and air dried to give 3.51 g (72%) of the product. The analytical sample was crystallized from EtOH/$H_2O$, m.p. 109–110° C.

D. 5-Amino-1-(2,6-dichloro-4-trifluoromethylphenyl)-4-(3-trifluoromethylbenzenesulfonyl)-3-methylthiopyrazole A suspension of 0.50 g (1.42 mmol) of 3,3-bis-methylthio-2-(3-trifluoromethylphenylsulfonyl)acrylonitrile and 0.35 g (1.42 mmol) of 2,6-dichloro-4-trifluoromethylphenylhydrazine in 10 mL of ethanol was heated at reflux for 2.5 hours, solution occurring as the reaction mixture was warmed. The mixture was stirred overnight at room temperature and was then poured into cold water. The product was extracted into ethyl acetate and the extracts were dried with magnesium sulfate and evaporated. The residues were crystallized from ether, and the product was filtered off and air dried to give 314 mg (40%) of the desired product, m.p. 201–203° C. Anal. Calcd. for $C_{18}H_{11}O_2N_3S_2Cl_2F_6$: C, 39.28; H, 2.02; N, 7.64. Found: C, 39.35; H, 2.19; N, 7.48.

E. 5-Dimethylamino-1-(2,6-dichloro-4-trifluoromethylphenyl)-4-(benzenesulfonyl)-3-methylthiopyrazole A solution of 0.241 g (0.5 mmol) of 5-amino-1-(2,6-dichloro-4-trifluoromethylphenyl)-4-(benzenesulfonyl)-3-methylthiopyrazole in 5 mL of dry dimethylsulfoxide was treated with 36 mg (1.5 mmol) of oil-free sodium hydride under dry nitrogen in a flame-dried flask at room temperature. After 30 minutes, a clear, pale yellow solution had formed. This solution was treated with 0.5 mL (8.0 mmol) of methyl iodide and stirred for 1 hour. Then the reaction mixture was poured into water and extracted twice with ethyl acetate. The combined extracts were dried with brine and with magnesium sulfate and evaporated. The residues crystallized from ether to give the desired product in 81% yield, m.p. 163–164° C.

EXAMPLE 16

The following compounds were prepared in accordance with Example 15.

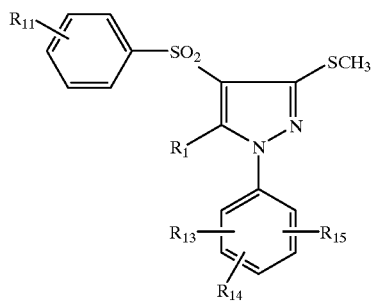

| $R_{11}$ | $R_{13},R_{14},R_{15}$ | $R_1$ | M.P. (° C.) or Analysis |
|---|---|---|---|
| H | 2,4,6-trichloro | $NH_2$ | 161–162 |
| H | 2,4,6-trichloro | $N(CH_3)_2$ | 200–202 |
| 2-(i-propyl) | 2,4,6-trichloro | $NH_2$ | 180–182 |
| 2-$OCH_3$ | 2,4,6-trichloro | $NH_2$ | 212–215 |
| 2-Cl | 2,4,6-trichloro | $NH_2$ | Anal. Calcd. for $C_{16}H_{11}O_2N_3S_2Cl_4$: C, 39.60; H, 2.39; N, 8.33. Found: C, 39.76; H, 229; N, 8.69 |
| H | 2,6-$Cl_2$-4-$CF_3$ | $NH_2$ | 209.5–210.5 |
| H | 2,6-$Cl_2$-4-$CF_3$ | $N(CH_3)_2$ | 163–164 |
| 3-$CF_3$ | 2,6-$Cl_2$-4-$CF_3$ | $NH_2$ | 201–203 |
| 3-$CF_3$ | 2,6-$Cl_2$-4-$CF_3$ | $N(CH_3)_2$ | 137–138 |

EXAMPLE 17

4-(2-Chlorophenyl)-1-(2,6-dichloro-4-trifluoromethylphenyl)-3-methylthiopyrazolo[3,4-d]pyrimidine A suspension of 669 mg (1.39 mmol) of 5-amino-1-(2,6-dichloro-4-trifluoromethylphenyl)-4-(2-chlorobenzoyl)-3-methylthiopyrazole in 5 mL of formamide was heated at 150° C. overnight. A pale yellow solid precipitated upon cooling of the reaction mixture. A total of 50 mL of water was added to the stirred suspension to complete the precipitation of the product which was filtered off and washed with water. An inseparable trace of starting material was observed in the product by thin layer chromatography (TLC) and so the above procedure was repeated on the mixture giving a brown solid containing no trace of starting material. Trituration of this solid with methylene chloride gave a pale yellow solution which was concentrated to give the desired product as a white crystalline solid, m.p. 156–158° C.

EXAMPLE 18

The following compounds were prepared in accordance with Example 17.

![structure]

| $R_3$ | $R_9$ | $R_{13}$ | m.p.(° C.) or HRMS |
|---|---|---|---|
| 2-Cl—Ph | H | Cl | 193–195 |
| 3-Cl—Ph | H | Cl | 171–173 |
| 2-Cl—Ph | H | $CF_3$ | 156–158 |
| 2-Cl—Ph | OH | Cl | 313–316 |
| 2-Cl—Ph | Cl | Cl | 193–195 |
| 2-Cl—Ph | 4-ethoxycarbonyl piperazinyl | Cl | 222–225 |
| 1-naphthyl | H | $CF_3$ | 171–173 |
| 2-Cl—Ph | $CH_3$ | Cl | 210–212 |
| 2-$CH_3$-5-iPrPh | $CH_3$ | Cl | 141–142 |
| 2,6-$(CH_3)_2$—Ph | $CH_3$ | Cl | HRMS Calcd. 462.0239. Found, 462.0369. |
| 2-$(OC_2H_5)$—Ph | $CH_3$ | Cl | 189.192 |
| 2-$(OC_2H_5)$-1-naphthyl | $CH_3$ | Cl | HRMS: Calcd.: 528.0345 Found: 528.0226 |
| 2-$OCH_3$—Ph | $CH_3$ | Cl | 214–216 |
| 2-$C_2H_5$—Ph | $CH_3$ | Cl | HRMS: Calcd. 462.0239 Found: 462.0219 |
| Ph | $CH_3$ | $CF_3$ | 114–116 |
| 2,5-$(CH_3)_2$—Ph | $CH_3$ | $CF_3$ | HRMS: Calcd. 497.0579 Found: 497.0602 |
| 2-$CF_3$—Ph | $CH_3$ | Cl | HRMS: Calcd. 501.9800 Found: 501.9778 |

We claim:

1. A compound of the formula

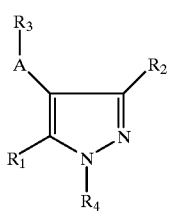

I wherein

A together with the carbons to which they are attached form 5-pyridyl which may be substituted by $R_5$ which is hydrogen, $C_1$–$C_6$ alkyl, fluoro, chloro, bromo, hydroxy, amino, $O(C_1$–$C_6$ alkyl), $NH(C_1$–$C_6$ alkyl), $N(C_1$–$C_6$ alkyl)($C_1$–$C_6$ alkyl), SH, $S(O)_n(C_1$–$C_6$ alkyl) wherein n=0, 1 or 2, wherein said $C_1$–$C_6$ alkyl may contain from one to two double or triple bonds and may be substituted by from 1 to 3 substituents $R_6$ which is hydroxy, amino, $C_1$–$C_3$ alkoxy, dimethylamino, diethylamino, methylamino, ethylamino, NH(C=O)$CH_3$, fluoro, chloro, bromo or $C_1$–$C_3$ thioalkyl; $R_2$ is hydrogen, $C_1$–$C_6$ alkyl, hydroxy, amino, $O(C_1$–$C_6$ alkyl), $NH(C_1$–$C_6$ alkyl), $N(C_1$–$C_6$ alkyl)($C_1$–$C_6$ alkyl), SH, $S(O)_n(C_1$–$C_6$ alkyl) wherein n=0, 1, or 2, cyano, hydroxy, carboxy, or amido, wherein said alkyls may be substituted by one to three of hydroxy, amino, carboxy, amido, NH(C=O)($C_1$–$C_6$ alkyl), $N(C_1$–$C_6$ alkyl)($C_1$–$C_6$ alkyl), (C=O)O($C_1$–$C_6$ alkyl), $C_1$–$C_3$ alkoxy, $C_1$–$C_3$ thioalkyl, fluoro, bromo, chloro, iodo, cyano or nitro; $R_3$ is phenyl, naphthyl or 3 to 8-membered cycloalkyl or 9 to 12 membered bicycloalkyl, wherein each one of the above groups may be substituted independently by from one to three of fluoro, chloro, bromo, trifluoromethyl, $C_1$–$C_6$ alkyl or $C_1$–$C_6$ alkoxy, or one of cyano, nitro, amino, $NH(C_1$–$C_6$ alkyl), $N(C_1$–$C_4$ alkyl)($C_1$–$C_2$ alkyl), COO ($C_1$–$C_4$ alkyl), CO($C_1$–$C_4$ alkyl), $SO_2NH(C_1$–$C_4$ alkyl), $SO_2N(C_1$–$C_4$ alkyl)($C_1$–$C_2$ alkyl), $SO_2NH_2$, $NHSO_2(C_1$–$C_4$ alkyl), $S(C_1$–$C_6$ alkyl), $SO_2(C_1$–$C_6$ alkyl), wherein said $C_1$–$C_4$ alkyl and $C_1$–$C_6$ alkyl may be substituted by one or two of fluoro, chloro, hydroxy, amino, methylamino, dimethylamino or acetyl; and $R_4$ is phenyl, naphthyl or 9 to 12-membered bicycloalkyl, wherein each of the above groups may be substituted independently by from one to three of fluoro, chloro, bromo, trifluoromethyl, $C_1$–$C_6$ alkyl or $C_1$–$C_6$ alkoxy, or one of cyano, nitro, amino, $NH(C_1$–$C_6$ alkyl), $N(C_1$–$C_4$ alkyl)($C_1$–$C_2$ alkyl), COO($C_1$–$C_4$ alkyl), CO($C_1$–$C_4$ alkyl), $SO_2NH(C_1$–$C_4$ alkyl), $SO_2N(C_1$–$C_4$ alkyl)($C_1$–$C_2$ alkyl), $SO_2NH_2$, $NH_2SO_2(C_1$–$C_4$ alkyl), $S(C_1$–$C_6$ alkyl), $SO_2(C_1$–$C_6$ alkyl), wherein said $C_1$–$C_4$ alkyl and $C_1$–$C_6$ alkyl may be substituted by one or two of fluoro, chloro, hydroxy, amino, methylamino, dimethylamino or acetyl; provided that $R_4$ is not unsubstituted phenyl; and provided that when $R_1$ is amino, $R_2$ is methylthio, $R_4$ is 2,4,6-trichlorophenyl, and A is C=O, then $R_3$ is not 2-chlorophenyl.

2. A compound according to claim 1 wherein $R_3$ is phenyl substituted independently with one or two of fluoro, chloro, bromo, methyl, trifluoromethyl, nitro, $C_1$–$C_6$ alkyl, $C_1$–$C_6$ alkyloxy, $SO_2NH_2$, $SO_2NH(C,-C,$ alkyl), $SO_2N(C_1$–$C_6$ alkyl)$_2$, or $R_3$ is primary, secondary or tertiary alkyl of from 4–9 carbon atoms wherein said $C_4$–$C_9$ alkyl may contain from one to two double or triple bonds and may be substituted by from 1 to 3 substituents $R_6$ which is hydroxy, amino, $C_1$–$C_3$ alkoxy, dimethylamino, diethylamino, methylamino, ethylamino, NH(C=O)$CH_3$, fluoro, chloro, bromo, or $C_1$–$C_3$ thioalkyl.

3. A compound according to claim 1 wherein $R_4$ is 2,4,6-trichlorophenyl, 2,4,6-trimethylphenyl, 2,6-dichloro-4-trifluoromethylphenyl or 4-bromo-2,6-dimethylphenyl.

4. A compound according to claim 1, wherein $R_2$ is methylthio or ethyl.

* * * * *